United States Patent
Iwai et al.

(10) Patent No.: US 7,776,510 B2
(45) Date of Patent: Aug. 17, 2010

(54) RESIST COMPOSITION, METHOD OF FORMING RESIST PATTERN, COMPOUND AND ACID GENERATOR

(75) Inventors: Takeshi Iwai, Kawasaki (JP); Hideo Hada, Kawasaki (JP); Keita Ishiduka, Kawasaki (JP); Akiya Kawaue, Kawasaki (JP); Hiroaki Shimizu, Kawasaki (JP); Kyoko Ohshita, Kawasaki (JP); Tsuyoshi Nakamura, Kawasaki (JP); Komei Hirahara, Kawasaki (JP); Yuichi Suzuki, Kawasaki (JP); Takehiro Seshimo, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 12/135,680

(22) Filed: Jun. 9, 2008

(65) Prior Publication Data

US 2008/0311522 A1    Dec. 18, 2008

(30) Foreign Application Priority Data

Jun. 13, 2007  (JP)  ............................ 2007-156556
Nov. 13, 2007  (JP)  ............................ 2007-294429

(51) Int. Cl.
*G03F 7/004* (2006.01)
*G03F 7/30* (2006.01)
*C07C 381/12* (2006.01)

(52) U.S. Cl. .................... 430/270.1; 430/326; 430/910; 430/922; 568/77

(58) Field of Classification Search .............. 430/270.1, 430/326, 910, 921; 568/77
See application file for complete search history.

(56) References Cited

U.S. PATENT DOCUMENTS

| | | | | |
|---|---|---|---|---|
| 5,679,496 A | * | 10/1997 | Ohsawa et al. | ............ 430/270.1 |
| 5,945,517 A |   | 8/1999  | Nitta et al. | |
| 6,106,993 A | * | 8/2000  | Watanabe et al. | ......... 430/270.1 |
| 6,180,313 B1|   | 1/2001  | Yukawa et al. | |
| 6,495,306 B2| * | 12/2002 | Uetani et al. | .............. 430/270.1 |
| 6,537,726 B2| * | 3/2003  | Nakanishi et al. | ......... 430/270.1 |
| 6,899,989 B2| * | 5/2005  | Suzuki et al. | ............. 430/270.1 |
| 7,323,287 B2|   | 1/2008  | Iwai et al. | |

FOREIGN PATENT DOCUMENTS

| | | |
|---|---|---|
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2003-241385 | 8/2003 |
| JP | 2005-37888 | 2/2005 |
| KR | 10-1999-0073776 A | 10/1999 |
| KR | 10-2002-0082006 A | 10/2002 |
| WO | WO 2004/074242 | 9/2004 |

OTHER PUBLICATIONS

Office Action issued on counterpart Korean Patent Application No. 10-2008-0054049, dated Nov. 19, 2009, Abstract.

* cited by examiner

*Primary Examiner*—John S Chu
(74) *Attorney, Agent, or Firm*—Knobbe, Martens, Olson & Bear, LLP

(57) ABSTRACT

A compound represented by general formula (b-14); and acid generator consisting of the compound; and a resist composition including a base component (A) which exhibits changed solubility in an alkali developing solution under action of acid and an acid-generator component (B) which generates acid upon exposure, the acid-generator component (B) including an acid generator (B1) consisting of a compound represented by general formula (b1-14):

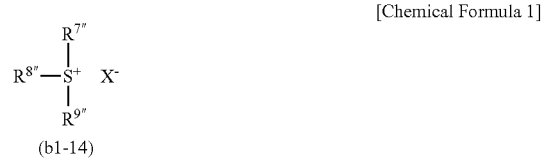

(b1-14)

wherein $R^{7\prime\prime}$ to $R^{9\prime\prime}$ each independently represents an aryl group or an alkyl group, wherein two of $R^{7\prime\prime}$ to $R^{9\prime\prime}$ may be bonded to each other to form a ring with the sulfur atom, and at least one of $R^{7\prime\prime}$ to $R^{9\prime\prime}$ represents a substituted aryl group in which a portion or all of the hydrogen atoms are substituted with an alkoxyalkyloxy group or an alkoxycarbonylalkyloxy group; and $X^-$ represents an anion.

12 Claims, No Drawings

RESIST COMPOSITION, METHOD OF FORMING RESIST PATTERN, COMPOUND AND ACID GENERATOR

RELATED APPLICATIONS

This application claims priority to Japanese Patent Application No. 2007-156556, filed Jun. 13, 2007, and Japanese Patent Application No. 2007-294429, filed Nov. 13, 2007, the contents of which are incorporated herein by reference.

TECHNICAL FIELD

The present invention relates to a resist composition, a method of forming a resist pattern using the resist composition, a compound useful as an acid generator for the resist composition, and the acid generator.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use exposure light source having a wavelength shorter than these excimer lasers, such as $F_2$ excimer lasers, electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist is used, which includes a base resin that exhibits a changed solubility in an alkali developing solution under action of acid and an acid generator that generates acid upon exposure. For example, a chemically amplified positive resist contains, as a base resin, a resin which exhibits increased solubility in an alkali developing solution under action of acid, and an acid generator. In the formation of a resist pattern, when acid is generated from the acid generator upon exposure, the exposed portions become alkali soluble.

Until recently, polyhydroxystyrene (PHS) or derivative resins thereof in which the hydroxyl groups are protected with acid-dissociable, dissolution-inhibiting groups (PHS-based resins), which exhibit high transparency to a KrF excimer laser (248 nm), have been used as the base resin component of chemically amplified resists. However, because PHS-based resins contain aromatic rings such as benzene rings, their transparency is inadequate for light with wavelengths shorter than 248 nm, such as light of 193 nm. Accordingly, chemically amplified resists that use a PHS-based resin as the base resin component suffer from low levels of resolution in processes that use light of 193 nm.

As a result, resins that contain structural units derived from (meth)acrylate esters within the main chain (acrylic resins) are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl (meth)acrylate are mainly used (for example, see Patent Document 1).

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

On the other hand, as acid generators usable in a chemically amplified resist, various types have been proposed including, for example, onium salt-based acid generators such as iodonium salts and sulfonium salts; oxime sulfonate-based acid generators; diazomethane-based acid generators; nitrobenzylsulfonate-based acid generators; iminosulfonate-based acid generators; and disulfone-based acid generators. Currently, as acid generators, those which include a triphenylsulfonium skeleton, dinaphthyl monophenylsulfonium skeleton, or the like are used (for example, see Patent Document 2).

[Patent Document 1] Japanese Unexamined Patent Application, First Publication No. 2003-241385
[Patent Document 2] Japanese Unexamined Patent Application, First Publication No. 2005-37888

DISCLOSURE OF INVENTION

Problems to be Solved by the Invention

In recent years, as requirements for high resolution increase with progress in the miniaturization of resist patterns, improvement in various lithography properties has been demanded.

For example, improvement in the pattern shape and mask reproducibility of a resist pattern formed becomes more important as the pattern size becomes smaller. Mask error factor (MEF) is a yardstick for indicating such a characteristic. More specifically, MEF is a parameter that indicates how faithfully mask patterns of differing dimensions can be reproduced (mask reproducibility) by using the same exposure dose with fixed pitch and changing the mask size (e.g., line width of a line and space pattern or hole diameter of a contact hole pattern). In the improvement of lithography properties, improvement of the pattern shape and MEF is important, and it is considered that this object can be achieved by using a novel acid generator.

The present invention takes the above circumstances into consideration, with an object of providing a novel compound preferable as an acid generator for a resist composition, an acid generator including the compound, a resist composition containing the acid generator, and a method of forming a resist pattern using the resist composition.

Means to Solve the Problems

For solving the above-mentioned problems, the present invention employs the following aspects. A first aspect of the present invention is a resist composition including a base component (A) which exhibits changed solubility in an alkali developing solution under action of acid and an acid-generator component (B) which generates acid upon exposure, the acid-generator component (B) including an acid generator (B1) consisting of a compound represented by general formula (b1-14).

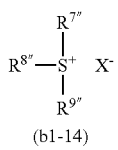

[Chemical Formula 1.]

(b1-14)

wherein $R^{7\prime\prime}$ to $R^{9\prime\prime}$ each independently represents an aryl group or an alkyl group, wherein two of $R^{7\prime\prime}$ to $R^{9\prime\prime}$ may be bonded to each other to form a ring with the sulfur atom, and at least one of $R^{7\prime\prime}$ to $R^{9\prime\prime}$ represents a substituted aryl group in which a portion or all of the hydrogen atoms are substituted with an alkoxyalkyloxy group or an alkoxycarbonylalkyloxy group; and $X^-$ represents an anion.

Further, a second aspect of the present invention is a method of forming a resist pattern, including: applying a resist composition of the above-mentioned first aspect of the present invention to a substrate to form a resist film on the substrate; conducting exposure of the resist film; and alkali-developing the resist film to form a resist pattern.

Furthermore, a third aspect of the present invention is a compound represented by general formula (b1-14) shown above.

Still further, a fourth aspect of the present invention is an acid generator consisting of a compound represented by general formula (b1-14) shown above.

In the present description and claims, the term "structural unit" refers to a monomer unit that contributes to the formation of a resin component (polymer).

The term "exposure" is used as a general concept that includes irradiation with any form of radiation.

An "alkyl group" includes linear, branched or cyclic, monovalent saturated hydrocarbon, unless otherwise specified.

A "lower alkyl group" is an alkyl group of 1 to 5 carbon atoms.

The term "acid dissociable, dissolution inhibiting group" refers to an organic group which can be dissociated by action of acid.

Effect of the Invention

According to the present invention, there are provided a resist composition, a method of forming a resist pattern using the resist composition, a novel compound preferable as an acid generator for the resist composition, and an acid generator consisting of the compound.

BEST MODE FOR CARRYING OUT THE INVENTION

Hereinbelow, the present invention will be described.

<<Compound of the Third Aspect>>

First, the compound of the third aspect of the present invention will be described. The compound of the third aspect of the present invention is represented by general formula (b1-14) shown above.

In general formula (b1-14), $R^{7\prime\prime}$ to $R^{9\prime\prime}$ each independently represents an aryl group or an alkyl group, wherein at least one of $R^{7\prime\prime}$ to $R^{9\prime\prime}$ represents a substituted aryl group in which a portion or all of the hydrogen atoms are substituted with an alkoxyalkyloxy group or an alkoxycarbonylalkyloxy group.

As the aryl group for $R^{7\prime\prime}$ to $R^{9\prime\prime}$, there is no particular limitation, and examples thereof include aryl groups of 6 to 20 carbon atoms in which a part or all of the hydrogen atoms may or may not be substituted with groups other than alkoxyalkyloxy groups and alkoxycarbonylalkyloxy groups, such as alkyl groups, alkoxy groups, halogen atoms or hydroxyl groups. The aryl group is preferably an aryl group having 6 to 10 carbon atoms because it can be synthesized at a low cost. Specific examples thereof include a phenyl group and naphthyl group.

The alkyl group, with which hydrogen atoms of the aryl group may be substituted, is preferably an alkyl group having 1 to 5 carbon atoms, and most preferably methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, and most preferably a methoxy group, ethoxy group, n-propoxy group, iso-propoxy group, n-butoxy group or tert-butoxy group.

The halogen atom, with which hydrogen atoms of the aryl group may be substituted, is preferably a fluorine atom.

The alkyl group for $R^{7\prime\prime}$ to $R^{9\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

At least one of $R^{7\prime\prime}$ to $R^{9\prime\prime}$ represents a substituted aryl group in which a portion or all of the hydrogen atoms are substituted with an alkoxyalkyloxy group or an alkoxycarbonylalkyloxy group. Two or more of $R^{7\prime\prime}$ to $R^{9\prime\prime}$ may be the aforementioned substituted aryl group, although it is particularly desirable that one of $R^{7\prime\prime}$ to $R^{9\prime\prime}$ be the aforementioned substituted aryl group.

As the alkoxyalkyloxy group with which hydrogen atoms of the aryl group are substituted, for example, those represented by general formula (b14-1) shown below may be exemplified.

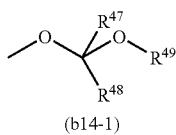

[Chemical Formula 2.]

(b14-1)

wherein $R^{47}$ and $R^{48}$ each independently represents a hydrogen atom or a linear or branched alkyl group, with the proviso that at least one of $R^{47}$ and $R^{48}$ represents a hydrogen atom; and $R^{49}$ represents an alkyl group, wherein $R^{48}$ and $R^{49}$ may be bonded to each other to form a ring structure.

In general formula (b14-1) above, $R^{47}$ and $R^{48}$ each independently represents a hydrogen atom or a linear or branched alkyl group, with the proviso that at least one of $R^{47}$ and $R^{48}$ represents a hydrogen atom.

The alkyl group for $R^{47}$ and $R^{48}$ preferably has 1 to 5 carbon atoms, and is preferably an ethyl group or a methyl group, and most preferably a methyl group.

It is preferable that either one of $R^{47}$ and $R^{48}$ be a hydrogen atom, and the other be a hydrogen atom or a methyl group, and it is particularly desirable that both of $R^{47}$ and $R^{48}$ be hydrogen atoms.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, ethyl group, propyl group, n-butyl group and tert-butyl group.

The cyclic alkyl group for $R^{49}$ preferably has 4 to 15 carbon atoms, more preferably 4 to 12 carbon atoms, and most preferably 5 to 10 carbon atoms.

Specific examples thereof include groups in which one or more hydrogen atoms have been removed from a monocycloalkane or a polycycloalkane such as a bicycloalkane, tricycloalkane or tetracycloalkane, and which may or may not be substituted with alkyl groups of 1 to 5 carbon atoms, fluorine atoms or fluorinated alkyl groups. Examples of the monocycloalkane include cyclopentane and cyclohexane. Examples of polycycloalkane include adamantane, norbornane, isobornane, tricyclodecane and tetracyclododecane. Among these, groups in which one or more hydrogen atoms have been removed from adamantane are preferable.

$R^{48}$ and $R^{49}$ may be bonded to each other to form a ring structure. In this case, a cyclic group is constituted of $R^{48}$, $R^{49}$, the oxygen atom to which $R^{49}$ is bonded, and the carbon atom to which the oxygen atom and $R^{48}$ are bonded. As the cyclic group, a 4- to 7-membered ring is preferable, and a 4- to 6-membered ring is more preferable.

As the alkoxycarbonylalkyloxy group with which hydrogen atoms of the aryl group are substituted, for example, those represented by general formula (b14-2) shown below may be exemplified.

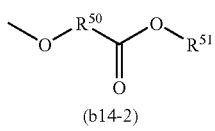

[Chemical Formula 3.]

(b14-2)

wherein $R^{50}$ represents a linear or branched alkylene group; and $R^{51}$ represents an acid dissociable group.

The linear or branched alkylene group for $R^{50}$ preferably has 1 to 5 carbon atoms, and examples thereof include a methylene group, ethylene group, trimethylene group, tetramethylene group and 1,1-dimethylethylene group.

The acid dissociable group for $R^{51}$ is not particularly limited as long as it is an organic group which can be dissociated by action of acid, and examples thereof include cyclic or chain-like tertiary alkyl ester-type acid dissociable groups and acetal-type acid dissociable groups such as alkoxyalkyl groups. Among these, tertiary alkyl ester-type acid dissociable groups are preferable. Specific examples thereof include 2-methyl-2-adamantyl group, 2-ethyl-2-adamantyl group, 1-methyl-1-cyclopentyl group, 1-ethyl-1-cyclopentyl group, 1-methyl-1-cyclohexyl group, 1-ethyl-1-cyclohexyl group, 1-(1-adamantyl)-1-methylethyl group, 1-(1-adamantyl)-1-methylpropyl group, 1-(1-adamantyl)-1-methylbutyl group, 1-(1-adamantyl)-1-methylpentyl group, 1-(1-cyclopentyl)-1-methylethyl group, 1-(1-cyclopentyl)-1-methylpropyl group, 1-(1-cyclopentyl)-1-methylbutyl group, 1-(1-cyclopentyl)-1-methylpentyl group, 1-(1-cyclohexyl)-1-methylethyl group, 1-(1-cyclohexyl)-1-methylpropyl group, 1-(1-cyclohexyl)-1-methylbutyl group, 1-(1-cyclohexyl)-1-methylpentyl group, tert-butyl group, tert-pentyl group and tert-hexyl group.

The number of the alkoxyalkyloxy group or alkoxycarbonylalkyloxy group with which hydrogen atoms of the substituted aryl group are substituted is preferably 2 or less, and most preferably 1.

The or each of $R^{7\prime\prime}$ to $R^{9\prime\prime}$ which is other than the aforementioned substituted aryl group is preferably a phenyl group or a naphthyl group, and most preferably a phenyl group.

Two of $R^{7\prime\prime}$ to $R^{9\prime\prime}$ may be bonded to each other to form a ring with the sulfur atom. In this case, it is preferable that the two of $R^{7\prime\prime}$ to $R^{9\prime\prime}$ form a 3 to 10-membered ring including the sulfur atom, and it is particularly desirable that the two of $R^{7\prime\prime}$ to $R^{9\prime\prime}$ form a 5 to 7-membered ring including the sulfur atom.

In general formula (b1-14) above, $X^-$ represents an anion. As the anion moiety of $X^-$, there is no particular limitation, and any anion moiety can be appropriately used which is known as an anion moiety of an onium salt-based acid generator. For example, an anion represented by general formula: $R^{14}SO_3^-$ (wherein $R^{14}$ represents a linear, branched or cyclic alkyl group, a halogenated alkyl group, an aryl group or an alkenyl group) or an anion represented by general formula: $R^1$—O—$Y^1$—$SO_3^-$ (wherein $R^1$ represents a monovalent aliphatic hydrocarbon group, a monovalent aromatic organic group or a monovalent hydroxyalkyl group; and $Y^1$ represents an alkylene group of 1 to 4 carbon atoms which may be fluorinated) can be used.

In general formula: $R^{14}SO_3^-$ above, $R^{14}$ represents a linear, branched or cyclic alkyl group, a halogenated alkyl group, an aryl group or an alkenyl group.

The linear or branched alkyl group for $R^{14}$ preferably has 1 to 10 carbon atoms, more preferably 1 to 8 carbon atoms, and most preferably 1 to 4 carbon atoms.

The cyclic alkyl group for $R^{14}$ preferably has 4 to 15 carbon atoms, more preferably 4 to 10 carbon atoms, and most preferably 6 to 10 carbon atoms.

The halogenated alkyl group for $R^{14}$ is an alkyl group in which a portion or all of hydrogen atoms are substituted with halogen atoms. The alkyl group is preferably a lower alkyl group of 1 to 5 carbon atoms, more preferably a linear or branched alkyl group, and still more preferably a methyl group, ethyl group, propyl group, isopropyl group, n-butyl group, tert-butyl group, tert-pentyl group or isopentyl group. Examples of the halogen atoms with which hydrogen atoms are substituted include fluorine atoms, chlorine atoms, bromine atoms and iodine atoms. In the halogenated alkyl group, it is preferable that 50 to 100% of the hydrogen atoms are substituted with halogen atoms, and it is more preferable that all hydrogen atoms are substituted with halogen atoms.

As the halogenated alkyl group, a fluorinated alkyl group is preferable. The fluorinated alkyl group preferably has 1 to 10 carbon atoms, more preferably 1 to 8 carbon atoms, and most preferably 1 to 4 carbon atoms. The fluorination ratio of the fluorinated alkyl group (percentage of the number of fluorine atoms substituting the hydrogen atoms within the alkyl group, based on the total number of hydrogen atoms within the alkyl group prior to fluorination, and the same applies to the fluorination ratio described below) is preferably from 10 to 100%, more preferably from 50 to 100%, and it is particularly desirable that all of the hydrogen atoms are substituted with fluorine atoms, as the acid strength increases. Specific examples of preferable fluorinated alkyl groups include a trifluoromethyl group, heptafluoro-n-propyl group and nonafluoro-n-butyl group.

The aryl group for $R^{14}$ is preferably an aryl group of 6 to 20 carbon atoms which may have a substituent. Examples of substituents include a halogen atom, a hetero atom and an alkyl group. The aryl group may have a plurality of substituents.

The alkenyl group for $R^{14}$ is preferably an alkenyl group of 2 to 10 carbon atoms which may have a substituent. Examples of substituents include a halogen atom, a hetero atom and an alkyl group. The alkenyl group may have a plurality of substituents.

Among these, as $R^{14}$, a halogenated alkyl group is preferable.

In general formula $R^1$—O—$Y^1$—$SO_3^-$ above, $R^1$ represents a monovalent aliphatic hydrocarbon group, a monovalent aromatic organic group or a monovalent hydroxyalkyl group; and $Y^1$ represents an alkylene group of 1 to 4 carbon atoms which may be fluorinated.

As the monovalent aliphatic hydrocarbon group for $R^1$, for example, a linear, branched or cyclic, monovalent saturated hydrocarbon group of 1 to 15 carbon atoms, or a linear or branched, monovalent unsaturated hydrocarbon group of 2 to 5 carbon atoms can be mentioned.

Examples of linear, monovalent saturated hydrocarbon groups include a methyl group, ethyl group, propyl group, butyl group, pentyl group, hexyl group, heptyl group, octyl group, nonyl group and decanyl group.

Examples of branched, monovalent saturated hydrocarbon groups include a 1-methylethyl group, 1-methylpropyl group, 2-methylpropyl group, 1-methybutyl group, 2-methylbutyl group, 3-methylbutyl group, 1-ethylbutyl group, 2-ethylbutyl group, 1-methylpentyl group, 2-methylpentyl group, 3-methylpentyl group and 4-methylpentyl group.

The cyclic, monovalent saturated hydrocarbon group may be either a polycyclic group or a monocyclic group. For example, groups in which one hydrogen atom has been removed from a monocycloalkane or a polycycloalkane such as a bicycloalkane, tricycloalkane or tetracycloalkane can be mentioned. Specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

Examples of linear, monovalent unsaturated hydrocarbon group include a vinyl group, propenyl group (allyl group) and butynyl group.

Examples of branched, monovalent unsaturated hydrocarbon group include 1-methylpropenyl group and 2-methylpropenyl group.

The monovalent aliphatic hydrocarbon group for $R^1$ preferably has 2 to 4 carbon atoms, and it is particularly desirable that the monovalent aliphatic hydrocarbon group have 3 carbon atoms.

Examples of monovalent aromatic organic groups for $R^1$ include aryl groups in which one hydrogen atom has been removed from an aromatic hydrocarbon ring, such as a phenyl group, a biphenyl group, a fluorenyl group, a naphthyl group, an anthracyl group, and a phenantryl group; heteroaryl groups in which some of the carbon atoms constituting the ring(s) of these groups are substituted with hetero atoms such as an oxygen atom, a sulfur atom, and a nitrogen atom; and arylalkyl groups such as a bezyl group, phenethyl group, 1-naphthylmethyl group, 2-naphthylmethyl group, 1-naphthylethyl group, and 2-naphthylethyl group. The alkyl chain within the arylalkyl group preferably has 1 to 4 carbon atoms, more preferably 1 or 2, and most preferably 1. These aryl groups, heteroaryl groups and arylalkyl groups may have a substituent such as an alkyl group of 1 to 10 carbon atoms, a halogenated alkyl group, an alkoxy group, a hydroxyl group or a halogen atom. The alkyl group or halogenated alkyl group as the substituent preferably has 1 to 8 carbon atoms, and more preferably 1 to 4 carbon atoms. The halogenated alkyl group is preferably a fluorinated alkyl group. Examples of halogen atoms include a fluorine atom, a chlorine atom, a bromine atom and an iodine atom, and a fluorine atom is preferable.

The monovalent hydroxyalkyl group for $R^1$ is a linear, branched or cyclic, monovalent saturated hydrocarbon group in which at least one hydrogen atom has been substituted with a hydroxyl group. Linear or branched, monovalent saturated hydrocarbon groups which one or two hydrogen atoms have been substituted with hydroxyl groups are preferable. Specific examples include a hydroxymethyl group, hydroxyethyl group, 1-hydroxypropyl group, 2-hydroxypropyl group, 3-hydroxypropyl group and 2,3-dihydroxypropyl group.

The monovalent hydroxyalkyl group for $R^1$ preferably has 1 to 10 carbon atoms, more preferably 1 to 8 carbon atoms, still more preferably 1 to 6, and most preferably 1 to 3 carbon atoms.

Examples of alkylene groups of 1 to 4 carbon atoms for $Y^1$ which may be fluorinated include —$CF_2$—, —$CF_2CF_2$—, —$CF_2CF_2CF_2$—, —$CF(CF_3)CF_2$—, —$CF(CF_2CF_3$—C$(CF_3)_2$—, —$CF_2CF_2CF_2CF_2$—, —$CF(CF_3)CF_2CF_2$—, —$CF_2CF(CF_3)CF_2$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH$(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)$CH_2$—, —$CH(CH_2CH_3)$—, —$C(CH_3)_2$—, —$CH_2CH_2CH_2CH_2$—, —$CH(CH_3)CH_2CH_2$—, —$CH_2CH$(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

As the alkylene group of 1 to 4 carbon atoms for $Y^1$ which may be fluorinated, it is preferable that the carbon atom bonded to S be fluorinated. Examples of such fluorinated alkylene groups include —$CF_2$—, —$CF_2CF_2$—, —$CF_2CF_2CF_2$—, —$CF(CF_3)CR_2$—, —$CF_2CF_2CF_2CF_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—; —CH$_2$CF$_2$—, —CH$_2$CH$_2$CF$_2$—, —CH$_2$CF$_2$CF$_2$—; —CH$_2$CH$_2$CH$_2$CF$_2$—, —CH$_2$CH$_2$CF$_2$CF$_2$—, and —CH$_2$CF$_2$CF$_2$CF$_2$—.

Among these, —CF$_2$CF$_2$—, —CF$_2$CF$_2$CF$_2$—, and CH$_2$CF$_2$CF$_2$— are preferable, —CF$_2$CF$_2$— and —CF$_2$CF$_2$CF$_2$— are more preferable, and —CF$_2$CF$_2$— is particularly desirable.

In general formula (b1-14) above, as X$^-$, anions represented by general formula (b-3) shown below and anions represented by general formula (b-4) shown below may be used.

[Chemical Formula 4.]

(b-3)    (b-4)

wherein X'' represents an alkylene group of 2 to 6 carbon atoms in which at least one hydrogen atom has been substituted with a fluorine atom; and Y'' and Z'' each independently represents an alkyl group of 1 to 10 carbon atoms in which at least one hydrogen atom has been substituted with a fluorine atom.

In general formula (b-3) above, X'' represents a linear or branched alkylene group in which at least one hydrogen atom has been substituted with a fluorine atom, and the alkylene group preferably has 2 to 6 carbon atoms, more preferably 3 to 5 carbon atoms, and most preferably 3 carbon atoms.

In general formula (b-4) above, Y'' and Z'' each independently represents a linear or branched alkyl group in which at least one hydrogen atom has been substituted with a fluorine atom, and the alkyl group preferably has 1 to 10 carbon atoms, more preferably 1 to 7 carbon atoms, and most preferably 1 to 3 carbon atoms.

The smaller the number of carbon atoms of the alkylene group for X'' or those of the alkyl group for Y'' and Z'' within the above-mentioned range of the number of carbon atoms, the more the solubility in a resist solvent is improved.

Further, in the alkylene group for X'' or the alkyl group for Y'' and Z'', it is preferable that the number of hydrogen atoms substituted with fluorine atoms is as large as possible because the acid strength increases and the transparency to high energy radiation of 200 nm or less or electron beam is improved. The fluorination ratio the alkylene group or alkyl group is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

In general formula (b1-14), X$^-$ may be a halogen anion. Examples of the halogen anion include a fluoride ion, a chloride ion, a bromide ion and an iodide ion.

Specific examples of the compound according to the third aspect of the present invention are shown below.

[Chemical Formula 5.]

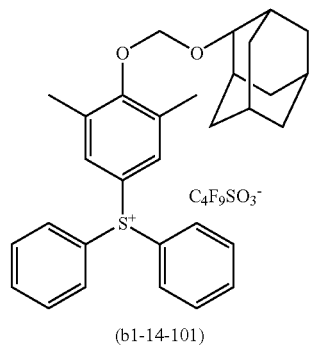

(b1-14-101)

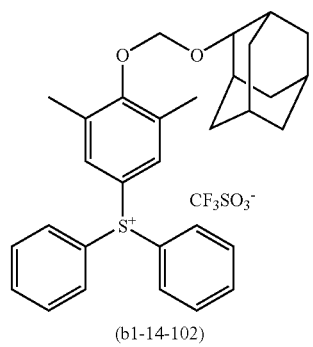

(b1-14-102)

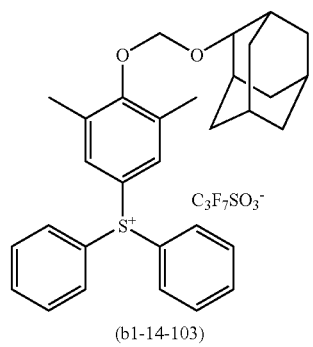

(b1-14-103)

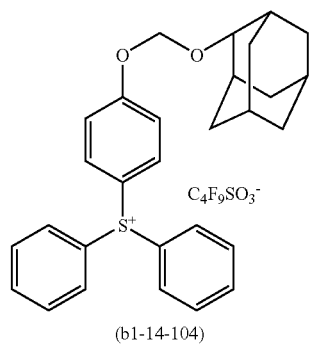

(b1-14-104)

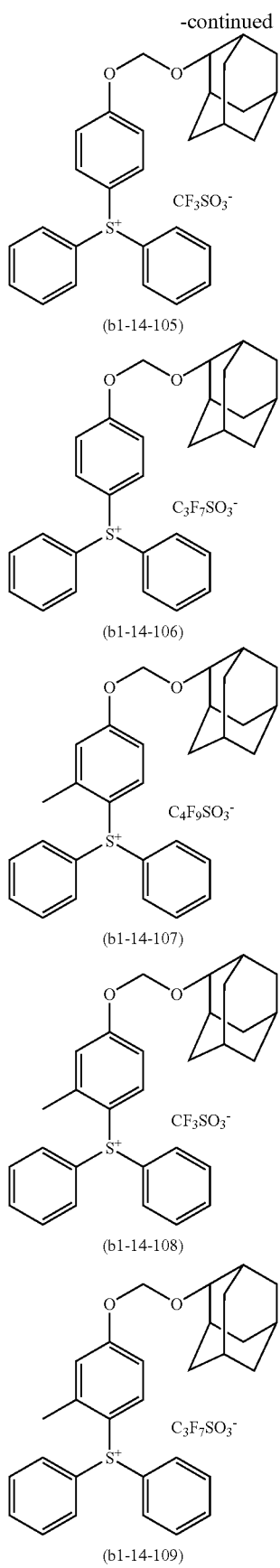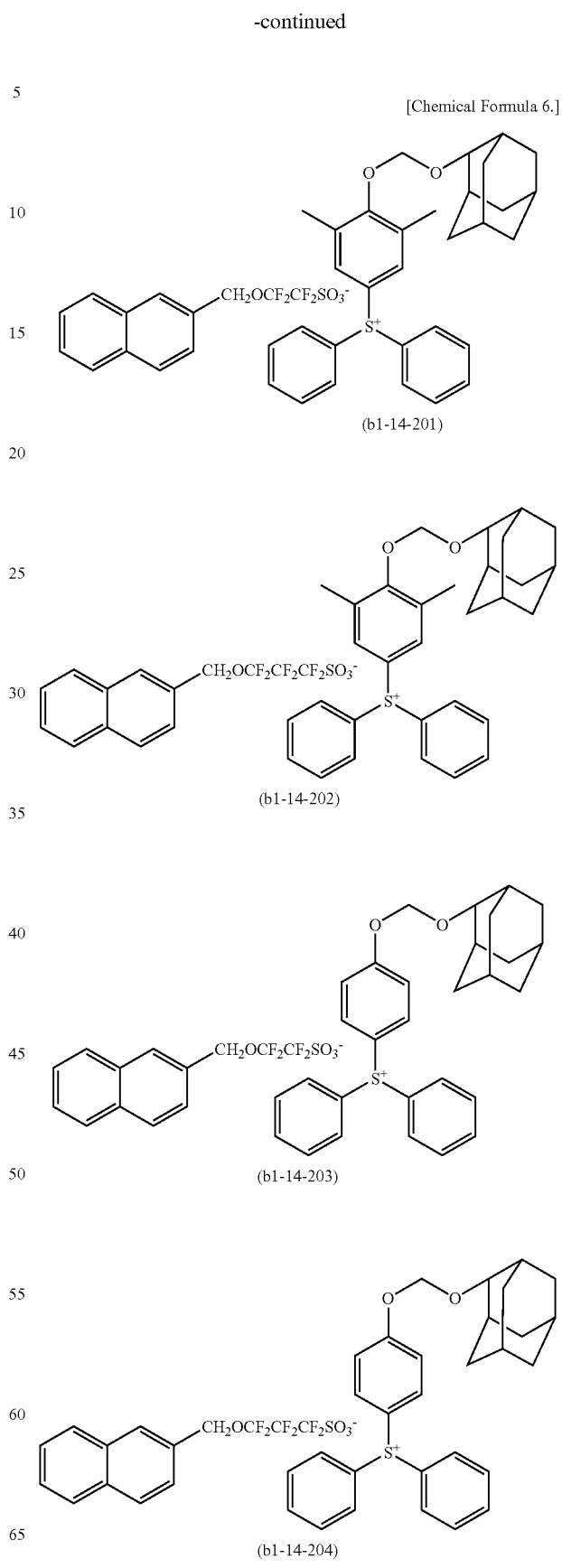

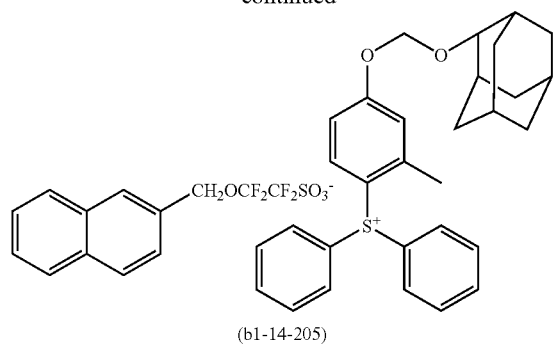
(b1-14-205)
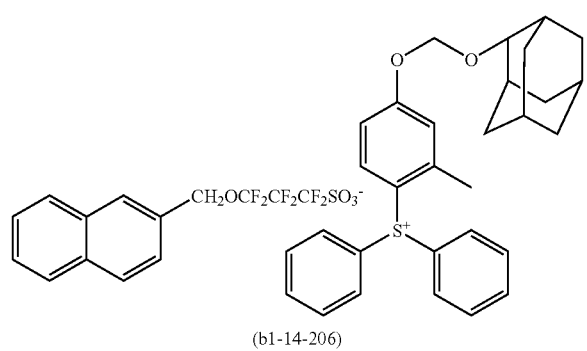
(b1-14-206)
[Chemical Formula 7.]
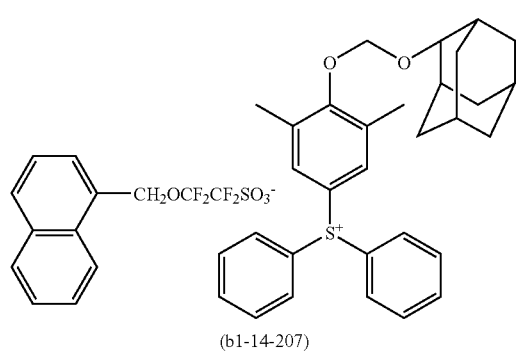
(b1-14-207)
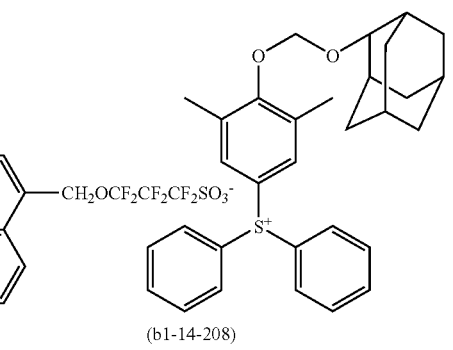
(b1-14-208)
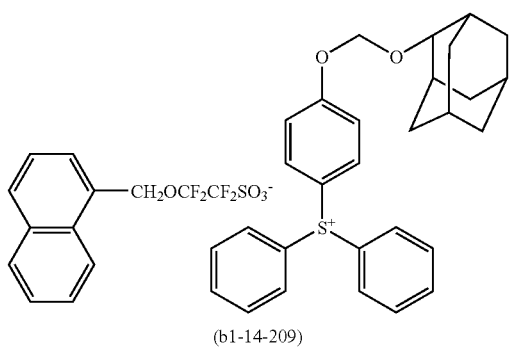
(b1-14-209)
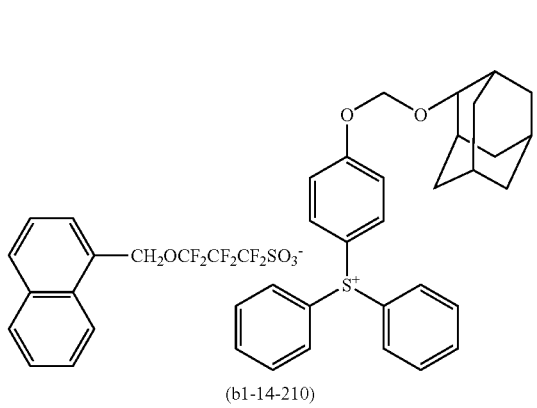
(b1-14-210)
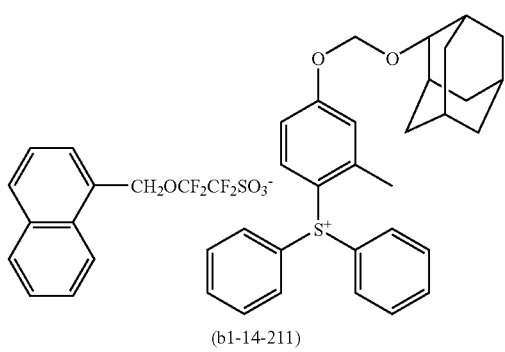
(b1-14-211)
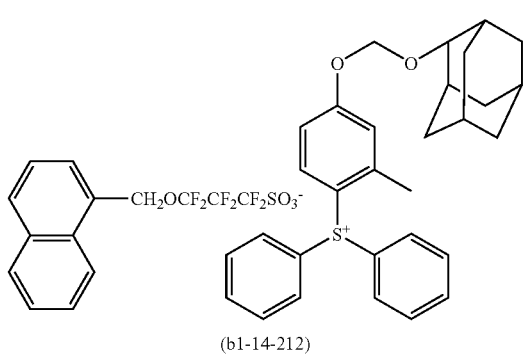
(b1-14-212)

-continued
[Chemical Formula 8.]
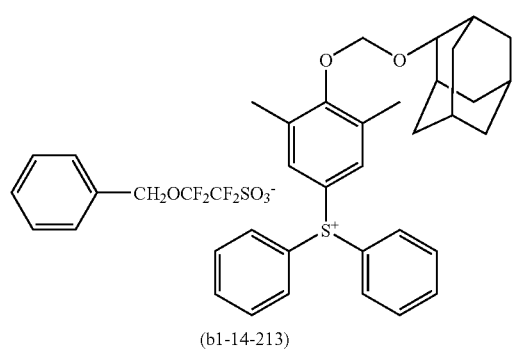
(b1-14-213)
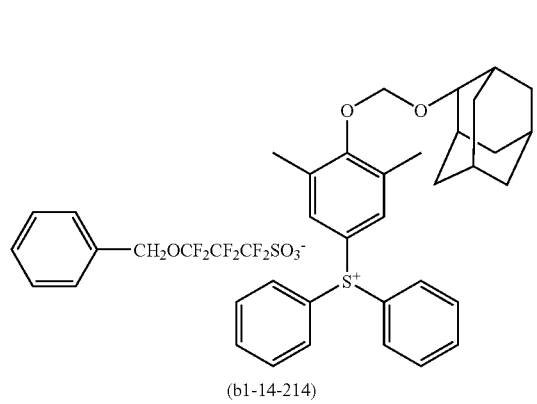
(b1-14-214)
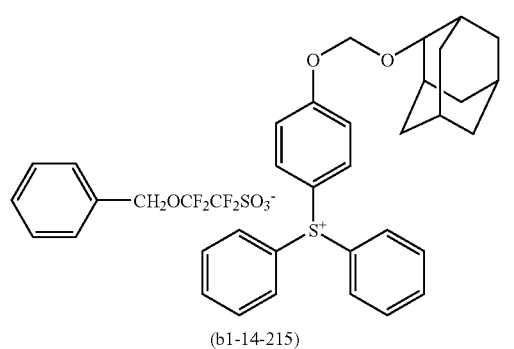
(b1-14-215)
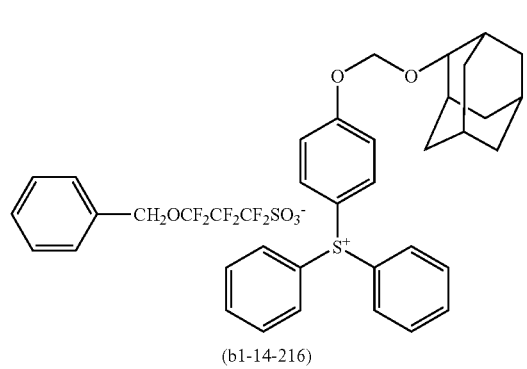
(b1-14-216)
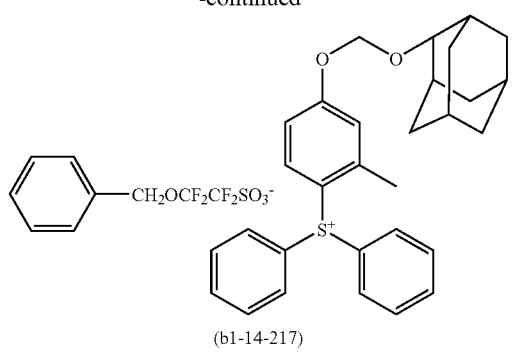
(b1-14-217)
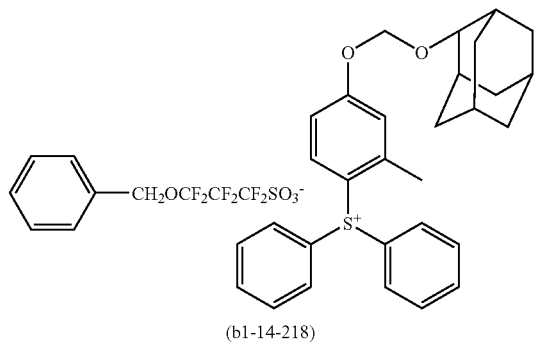
(b1-14-218)
[Chemical Formula 9.]
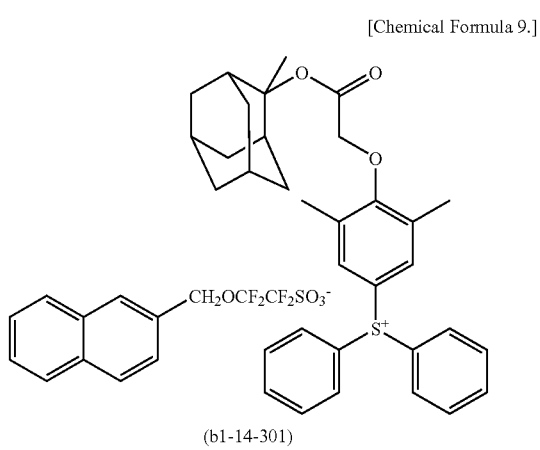
(b1-14-301)
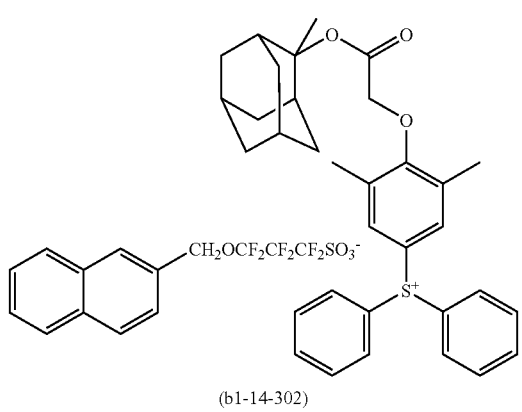
(b1-14-302)

-continued
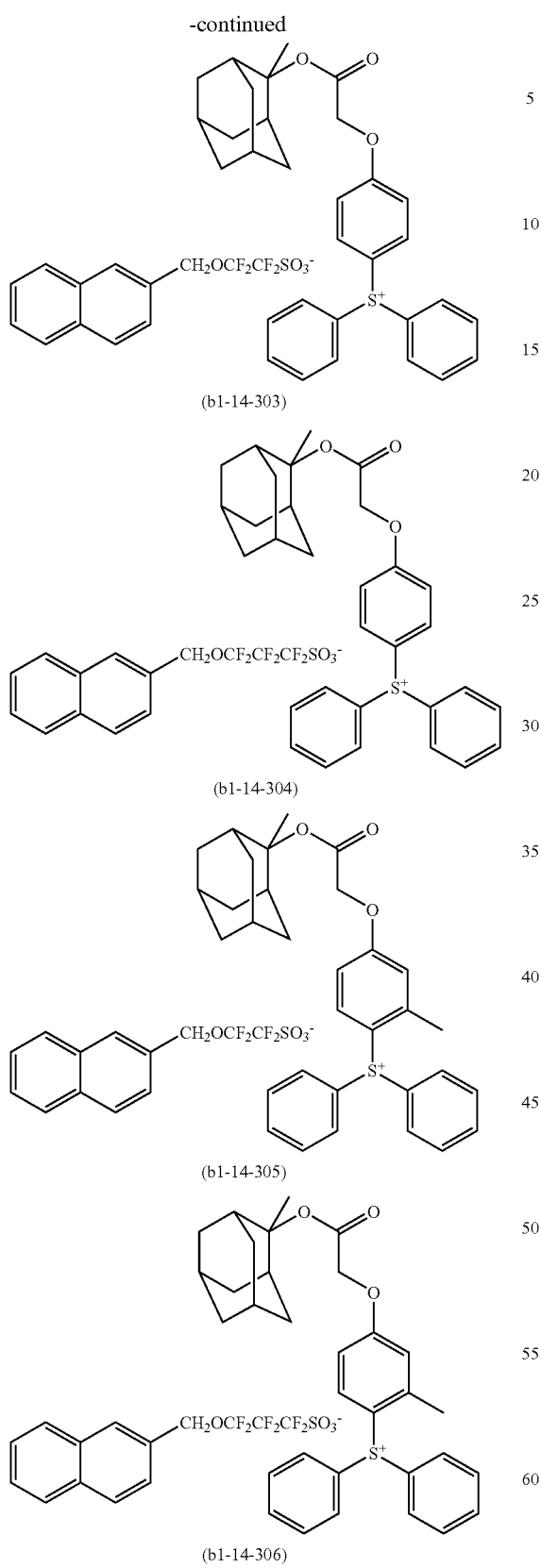
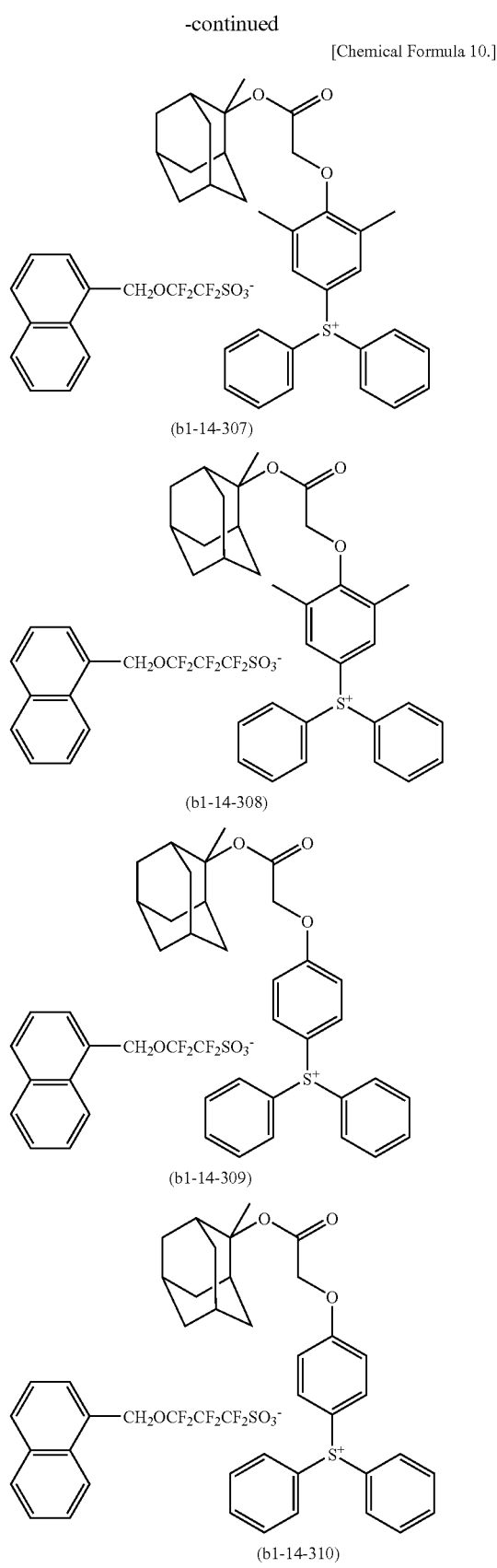

-continued
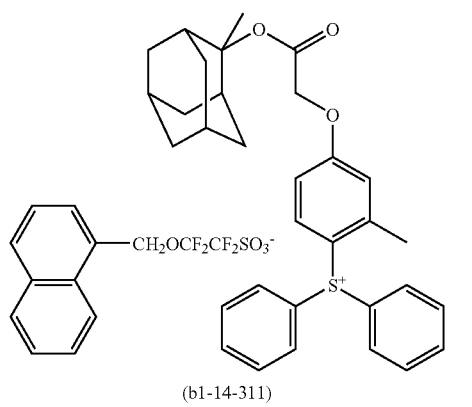
(b1-14-311)
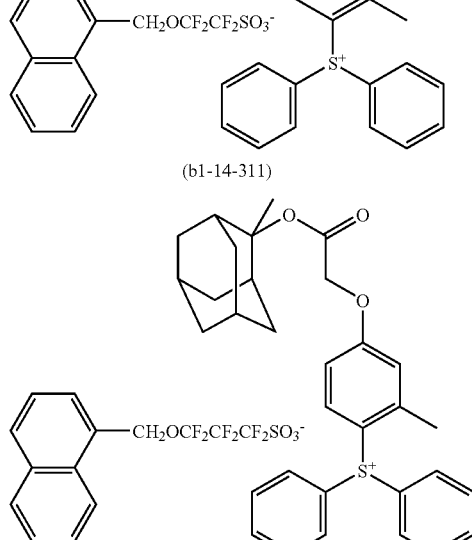
(b1-14-312)
[Chemical Formula 11.]
(b1-14-313)
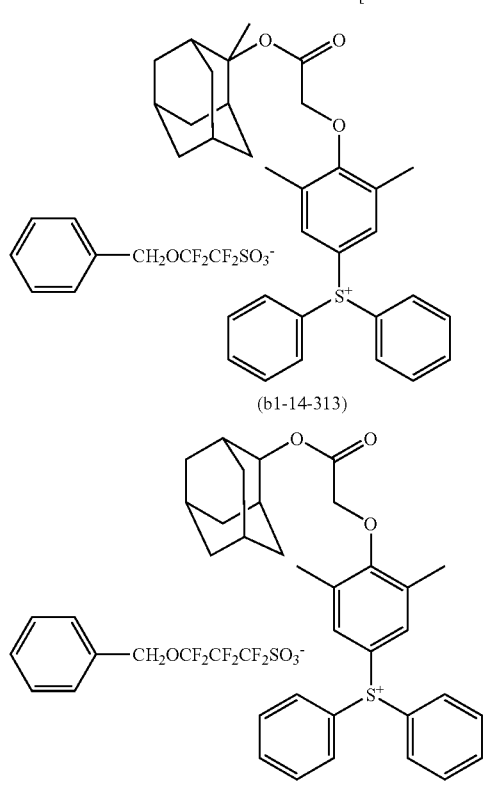
(b1-14-314)
-continued
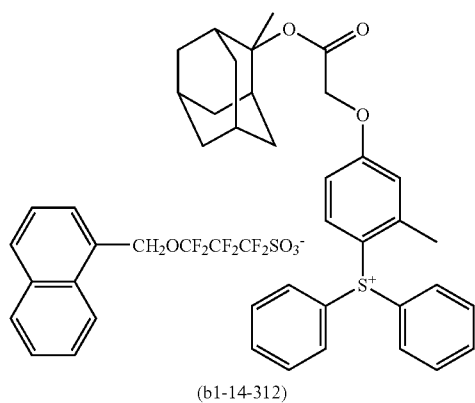
(b1-14-315)
(b1-14-316)
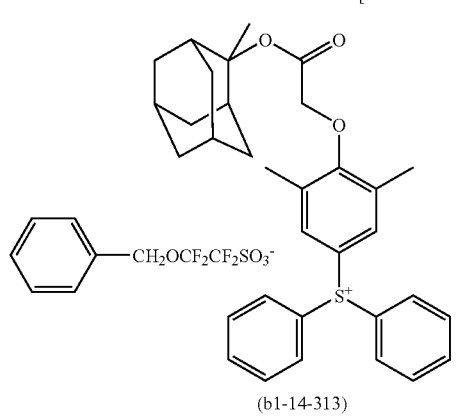
(b1-14-317)
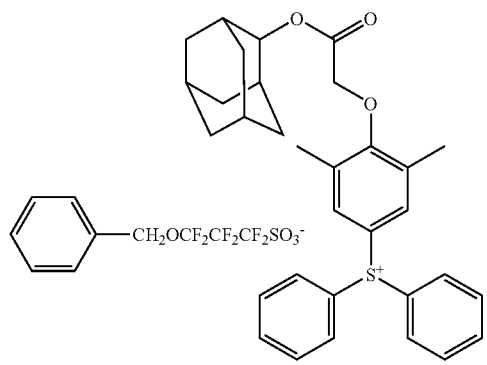
(b1-14-318)

-continued
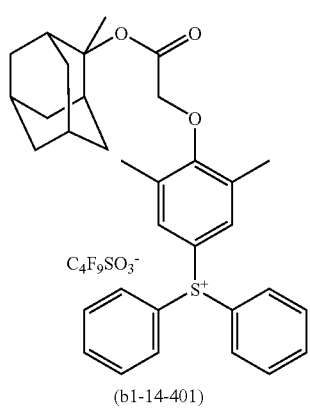
(b1-14-401)
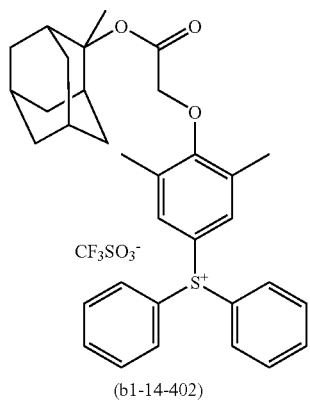
(b1-14-402)
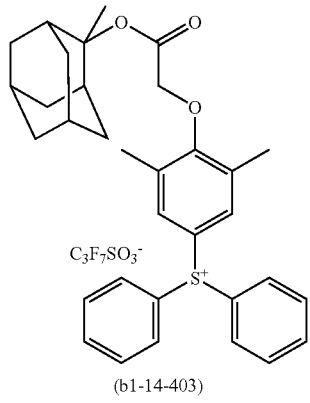
(b1-14-403)
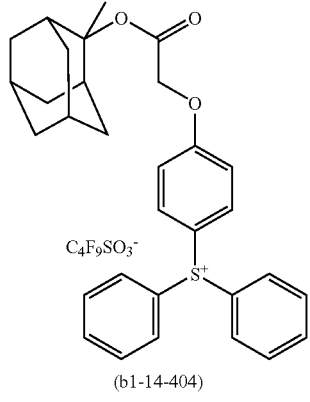
(b1-14-404)
[Chemical Formula 12.]
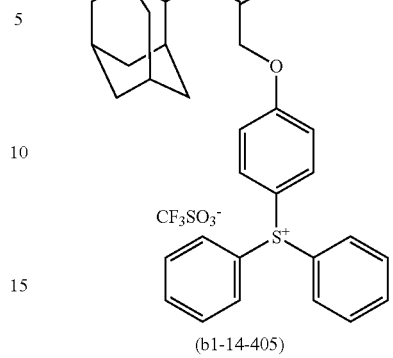
(b1-14-405)
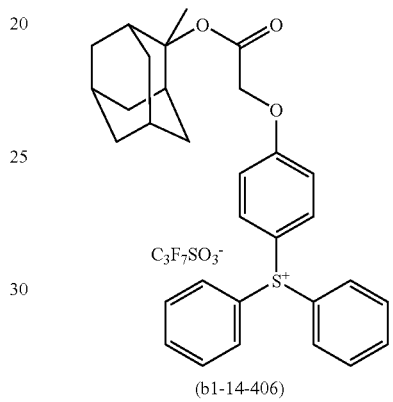
(b1-14-406)
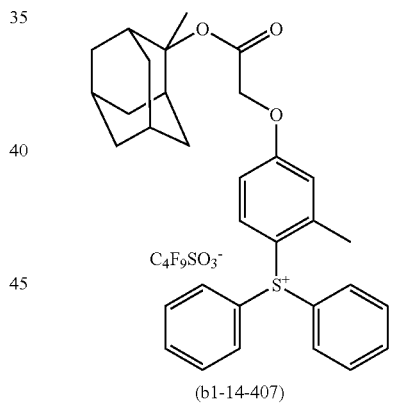
(b1-14-407)
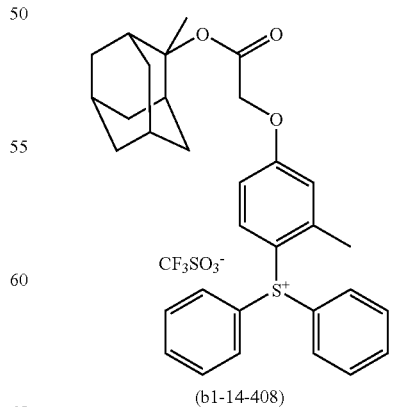
(b1-14-408)

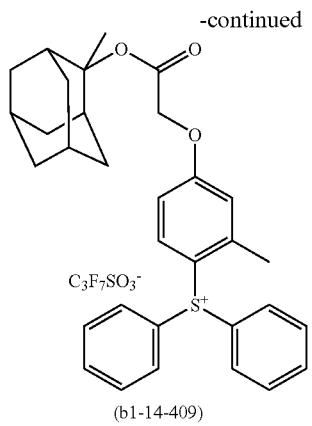

(b1-14-409)

Among these, compounds represented by formulas (b1-14-101), (b1-14-201), (b1-14-301), (b1-14-401) and (b1-14-402) above are preferable.

<Production Method of Compound of the Third Aspect>

The compound (b1-14) according to the third aspect of the present invention can be produced, for example, as follows. A compound represented by general formula (b1-14-01) shown below and a compound represented by general formula (b1-14-02) shown below are added to a solution of an organic acid H$^+$B$^-$ (wherein B$^-$ represents an anion moiety of an organic acid, such as methanesulfonic acid ion), and reacted. Then, pure water and an organic solvent (e.g., dichloromethane, tetrahydrofuran or the like) are added thereto, and the organic phase is collected, to thereby obtain a compound represented by general formula (b1-14-03) shown below from the organic phase.

Subsequently, the compound represented by general formula (b1-14-03) is dissolved in a mixed solvent of an organic solvent (e.g., dichloromethane, tetrahydrofuran or the like) and water. Then, an alkali metal salt L$^+$X$^-$ (wherein L$^+$ represents an alkali metal cation such as a lithium ion, potassium ion or sodium ion) having a desired anion X$^-$ is added thereto, and reacted. The resultant is subjected to liquid separation and washing with water, to thereby obtain a compound represented by general formula (b1-1 4-04) shown below from the organic phase.

Thereafter, the compound represented by general formula (b1-14-04) is dissolved in an organic solvent (e.g., dichloromethane, tetrahydrofuran or the like), and cooled with ice. Then, a base (e.g., sodium hydride, or the like) is added thereto, and a halogenide of a desired alkoxyalkyl group or alkoxycarbonylalkyl group (e.g., compounds represented by general formulas "Cl—C(R$^{47}$)(R$^{48}$)—O—R$^{49}$", "Cl—R$^{50}$—C(=O)—O—R$^{51}$", and "Br—R$^{50}$—C(=O)—O—R$^{51}$" (wherein R$^{47}$ to R$^{51}$ are as defined above)) is further added to substitute the hydrogen atom of the —OH group within —R$^{10'''}$—OH with the alkoxyalkyl group or alkoxycarbonylalkyl group, thereby obtaining the compound (b1-14).

[Chemical Formula 13.]

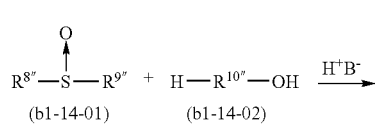

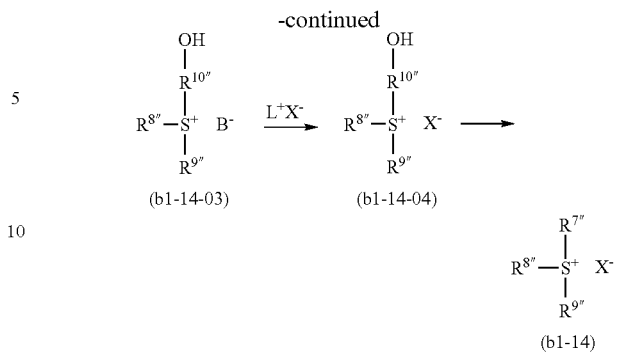

wherein R$^{8'''}$ and R$^{9'''}$ are the same as R$^{8'''}$ and R$^{9'''}$ in general formula (b1-14) above; R$^{10'''}$ represents an arylene group which is the aryl group for R$^{7'''}$ in general formula (b1-14) above having one hydrogen atom removed therefrom; B$^-$ represents an anion moiety of an organic acid; L$^+$ represents an alkali metal cation; and X$^-$ is the same as X$^-$ in general formula (b1-14) above.

Alternatively, the compound (b1-14) can be obtained as follows. The hydrogen atom of the —OH group within —R$^{10'''}$—OH in the compound (b1-14-03) may be substituted with the alkoxyalkyl group or alkoxycarbonylalkyl group prior to reacting the compound (b1-14-03) with L$^+$X$^-$, and then the anion exchange of the compound (b1-14-03) may be conducted, thereby obtaining the compound (b1-14).

<<Acid Generator of Fourth Aspect>>

The acid generator of the fourth aspect of the present invention (hereafter, frequently referred to as "acid generator (B1)") consists of a compound represented by general formula (b1-14) above. In general formula (b1-14), as R$^{7'''}$ to R$^{9'''}$ and X$^-$, the same as those described above in connection with the compound of the third aspect of the present invention can be exemplified.

<<Resist Composition of the First Aspect>>

Next, the resist composition of the first aspect of the present invention will be described. The resist composition of the first aspect of the present invention includes a base component (A) (hereafter, frequently referred to as "component (A)") which exhibits changed solubility in an alkali developing solution under action of acid and an acid-generator component (B) which generates acid upon irradiation, and the acid-generator component (B) (hereafter, frequently referred to as "component (B)") contains an acid generator (B 1) consisting of a compound represented by general formula (b1-14) shown above.

In the resist composition of the present invention, as the component (A), a polymeric material which exhibits changed solubility in an alkali developing solution under action of acid may be used. Alternatively, as the component (A), a low molecular weight material which exhibits changed solubility in an alkali developing solution under action of acid may be used.

Further, the resist composition of the present invention may be a negative resist composition or a positive resist composition.

When the resist composition of the present invention is a negative resist composition, for example, the component (A) is an alkali-soluble resin, and a cross-linking agent (C) is blended with the resist composition.

In the negative resist composition, during resist pattern formation, when acid is generated from the component (B)

upon exposure, the action of this acid causes cross-linking between the alkali-soluble resin and the cross-linking agent, and the cross-linked portion becomes alkali insoluble.

As the alkali-soluble resin, it is preferable to use a resin having a structural unit derived from at least one of α-(hydroxyalkyl)acrylic acid and a lower alkyl ester of a-(hydroxyalkyl)acrylic acid, as it enables formation of a satisfactory resist pattern with minimal swelling. Here, the term "α-(hydroxyalkyl) acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent (C), typically, an amino-based cross-linking agent such as a glycoluril having a methylol group or alkoxymethyl group is preferable, as it enables formation of a resist pattern with minimal swelling. The amount of the cross-linking agent (C) added is preferably within the range from 1 to 50 parts by weight, relative to 100 parts by weight of the alkali-soluble resin.

When the resist composition of the present invention is a positive resist composition, the component (A) is insoluble in an alkali developing solution prior to exposure, and during resist pattern formation, when acid is generated from the component (B) upon exposure, the acid dissociable, dissolution inhibiting groups of the component (A) are dissociated by the generated acid, and the solubility of the entire component (A) in an alkali developing solution increases, so that the component (A) changes from alkali insoluble to alkali soluble. Therefore, in the formation of a resist pattern, by conducting selective exposure of a resist film formed by applying the positive resist composition onto a substrate, the exposed portions become alkali soluble, whereas the unexposed portions remain alkali insoluble, and hence, a resist pattern can be formed by alkali developing.

In the resist composition of the present invention, the component (A) is preferably a base component which exhibits increased solubility in an alkali developing solution under action of acid. That is, the resist composition of the present invention is preferably a positive resist composition. Further, the component (A) is preferably a resin component (A1) (hereafter referred to as "component (A1)") which exhibits increased solubility in an alkali developing solution under action of acid.

<Component (A1)>

The component (A1) suitably used for such a positive resist composition preferably has a structural unit (a1) derived from an acrylate ester having an acid dissociable, dissolution inhibiting group.

Further, it is preferable that the component (A1) also has a structural unit (a2) derived from an acrylate ester having a lactone-containing cyclic group.

Furthermore, it is preferable that the component (A1) also has a structural unit (a3) derived from an acrylate ester having a polar group-containing aliphatic hydrocarbon group.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, ethyl group, propyl group, isopropyl group, n-butyl group, isobutyl group, tert-butyl group, pentyl group, isopentyl group, and neopentyl group.

Specific examples of the halogenated lower alkyl group include groups in which some or all of the hydrogen atoms of the aforementioned "lower alkyl group for the substituent at the α-position" are substituted with halogen atoms. Examples of halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

-Structural Unit (a1)

Structural unit (a1) is a structural unit derived from an acrylate ester containing an acid dissociable, dissolution inhibiting group.

As the acid-dissociable, dissolution-inhibiting group in the structural unit (a1), any of the groups that have been proposed as acid-dissociable, dissolution-inhibiting groups for the base resins of chemically amplified resists can be used, provided the group has an alkali dissolution-inhibiting effect that renders the entire component (A1) alkali-insoluble prior to dissociation, and then following dissociation by action of acid, causes the entire component (A1) to change to an alkali-soluble state.

Generally, groups that form either a cyclic or chain-like tertiary alkyl ester with the carboxyl group of the (meth) acrylate ester, and acetal-type acid dissociable, dissolution inhibiting groups such as alkoxyalkyl groups are widely known. In the present description, the term "(meth)acrylate ester" is a generic term that includes either or both of the acrylate ester having a hydrogen atom bonded to the α-position and the methacrylate ester having a methyl group bonded to the α-position.

Here, a tertiary alkyl ester describes a structure in which an ester is formed by substituting the hydrogen atom of a carboxyl group with a linear or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid-dissociable, dissolution-inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

In the present description and claims, the term "aliphatic" is a relative concept used in relation to the term "aromatic", and defines a group or compound that has no aromaticity.

The term "aliphatic branched" refers to a branched structure having no aromaticity.

The "aliphatic branched, acid dissociable, dissolution inhibiting group" is not limited to be constituted of only carbon and hydrogen (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be exemplified. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclodecanyl group, and a branched alkylene group having a tertiary carbon atom bonded thereto, as in the structural units represented by general formulas (a1"-1) to (a1"-6) shown below, can be exemplified.

[Chemical Formula 14.]

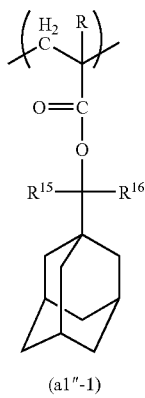

(a1"-1)

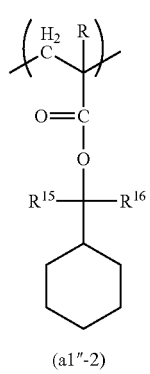

(a1"-2)

-continued

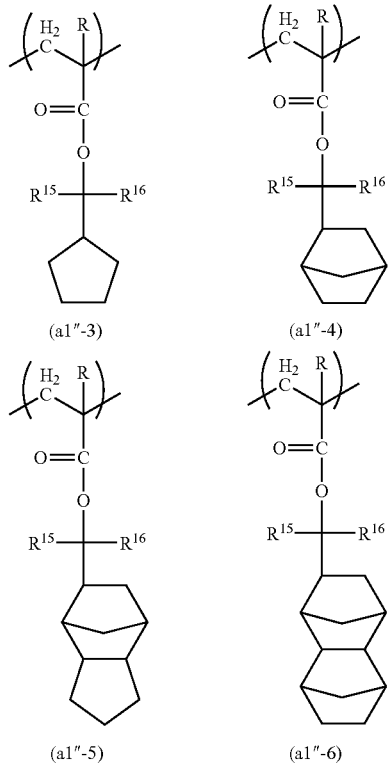

(a1"-3)  (a1"-4)

(a1"-5)  (a1"-6)

wherein R represents a hydrogen atom, a lower alkyl group or a halogenated lower alkyl group; and $R^{15}$ and $R^{16}$ each independently represents an alkyl group (which may be linear or branched, and preferably has 1 to 5 carbon atoms).

In general formulas (a1"-1) to (a1"-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" is generally substituted with a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 15.]

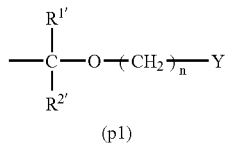

(p1)

wherein $R^{1\prime}$ and $R^{2\prime}$ each independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same as the lower alkyl groups for R above can be exemplified. As the lower alkyl group for $R^{1\prime}$ and $R^{2\prime}$, a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

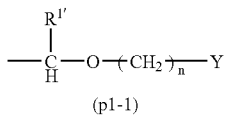

[Chemical Formula 16.]

(p1-1)

wherein $R^{1\prime}$, n and Y are as defined above.

As the lower alkyl group for Y, the same as the lower alkyl groups for R above can be exemplified.

As the aliphatic cyclic group for Y; any of the aliphatic monocyclic/polycyclic groups which have been proposed for conventional ArF resists and the like can be appropriately selected for use. For example, the same groups described above in connection with the "aliphatic cyclic group" can be exemplified.

Further, as the acetal-type, acid dissociable, dissolution inhibiting group, groups represented by general formula (p2) shown below can also be exemplified.

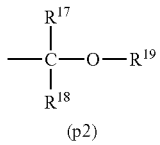

[Chemical Formula 17.]

(p2)

wherein $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be exemplified. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

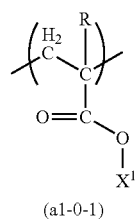

[Chemical Formula 18.]

(a1-0-1)

wherein R represents a hydrogen atom, a lower alkyl group or a halogenated lower alkyl group; and $X^1$ represents an acid dissociable, dissolution inhibiting group.

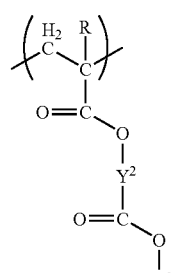

[Chemical Formula 19.]

(a1-0-2)

wherein R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.

In general formula (a1-0-1) shown above, lower alkyl group and halogenated lower alkyl group for R are the same as the lower alkyl group and halogenated lower alkyl group which can be bonded to the x-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined above.

$X^2$ is the same as $X^1$ in general formula (a1-0-1).

$Y^2$ is preferably an alkylene group of 1 to 10 carbon atoms or a divalent aliphatic cyclic group. As the aliphatic cyclic group, the same as those exemplified above in connection with the explanation of "aliphatic cyclic group" can be used, except that two hydrogen atoms have been removed therefrom.

Specific examples of the structural unit (a1) include structural units represented by general formulas (a1-1) to (a1-4) shown below.

[Chemical Formula 20.]

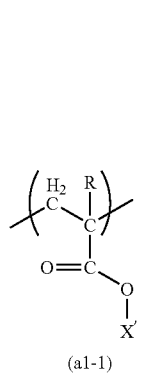
(a1-1)

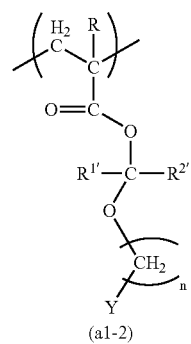
(a1-2)

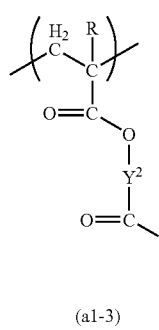
(a1-3)

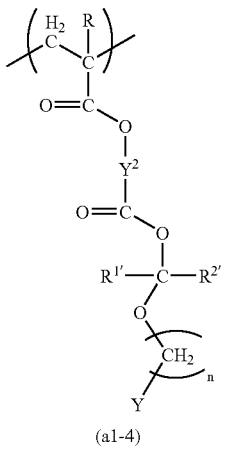
(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group or an aliphatic cyclic group; R is as defined above; and $R^{1'}$ and $R^{2'}$ each independently represents a hydrogen atom or a lower alkyl group of 1 to 5 carbon atoms.

It is preferable that at least one of $R^{1'}$ and $R^{2'}$ represent a hydrogen atom, and it is more preferable that both of $R^{1'}$ and $R^{2'}$ represent a hydrogen atom. n is preferably 0 or 1.

Examples of the tertiary alkyl ester-type acid dissociable, dissolution inhibiting group for X' are the same as the above-exemplified tertiary alkyl ester-type acid dissociable, dissolution inhibiting groups for $X^1$.

Examples of the aliphatic cyclic group for Y are the same as those exemplified above in connection with the explanation of "aliphatic cyclic group".

$Y^2$ is preferably an alkylene group of 1 to 10 carbon atoms or a divalent aliphatic cyclic group. As the aliphatic cyclic group, the same as those exemplified above in connection with the explanation of "aliphatic cyclic group" can be used, except that two hydrogen atoms have been removed therefrom. When $Y^2$ represents an alkylene group of 1 to 10 carbon atoms, it is more preferable that the number of carbons is 1 to 6, still more preferably 1 to 4, and most preferably 1 to 3. When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

Specific examples of structural units represented by general formula (a1-1) to (a1-4) are shown below.

[Chemical Formula 21.]

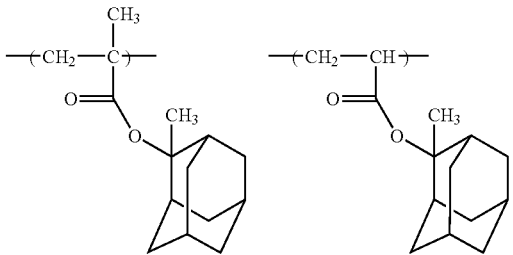
(a1-1-1)  (a1-1-2)

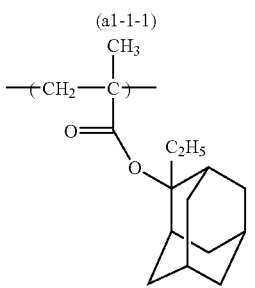
(a1-1-3)

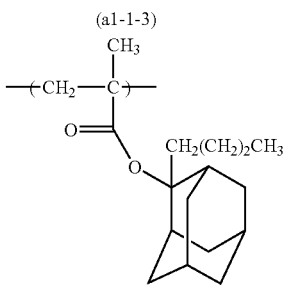
(a1-1-4)

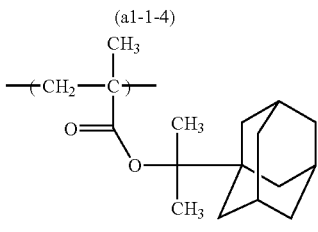
(a1-1-5)

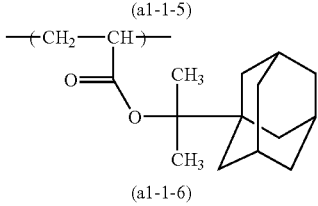
(a1-1-6)

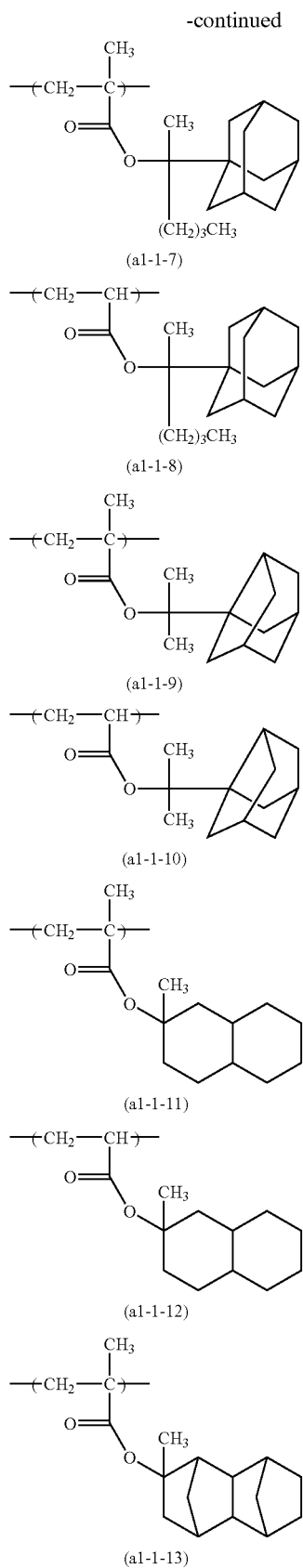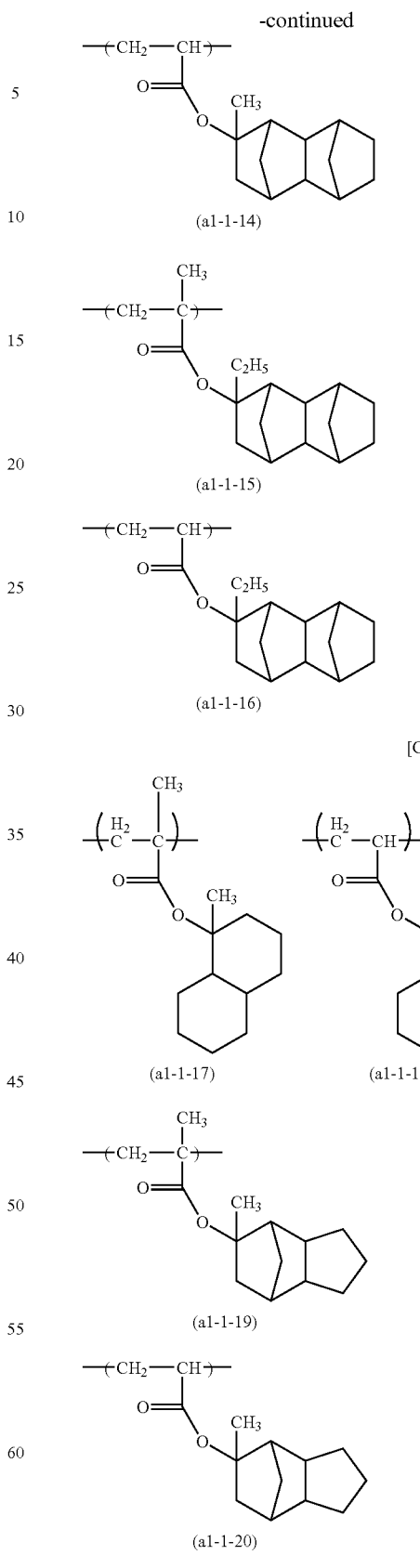
[Chemical Formula 22.]

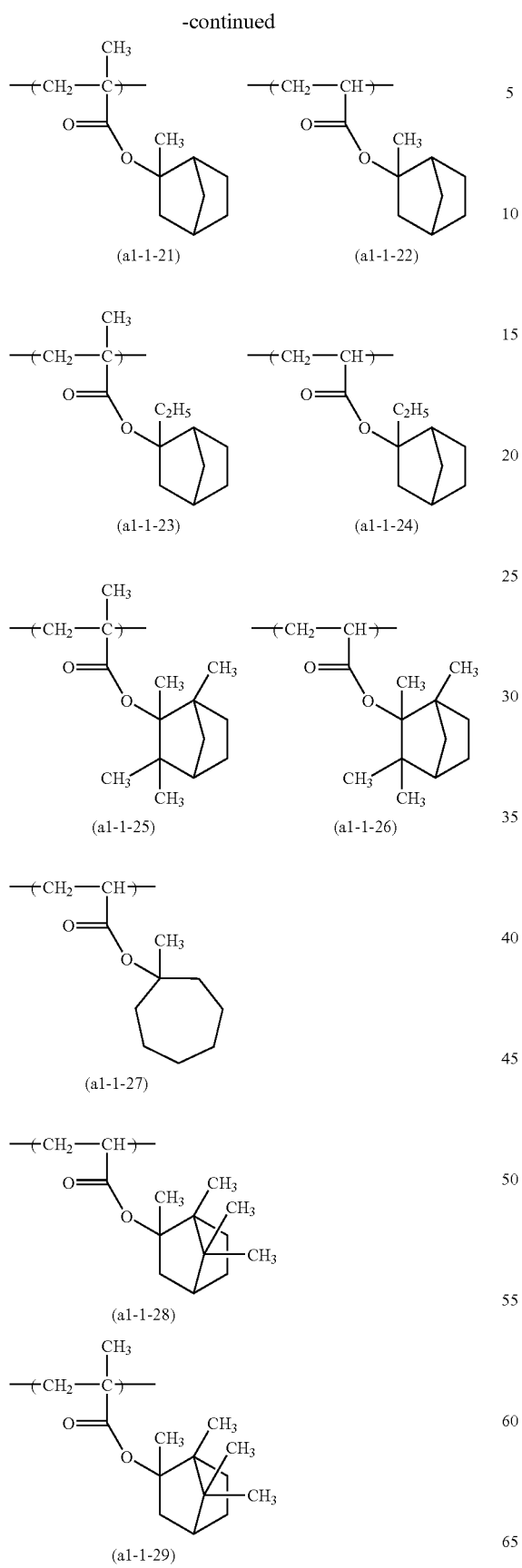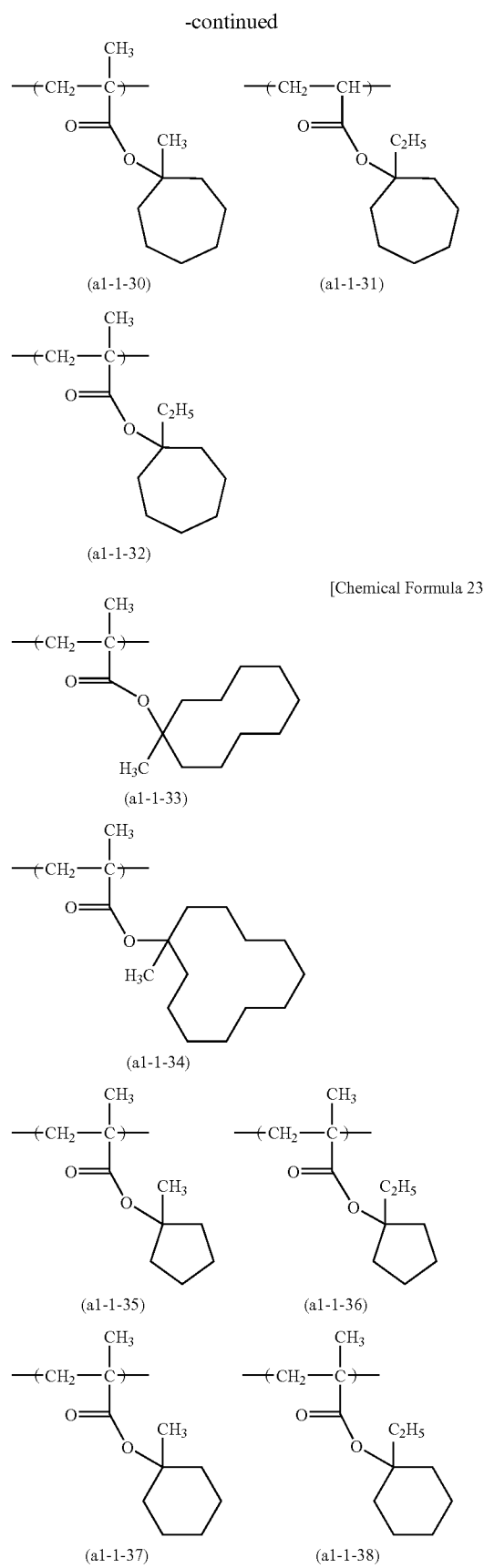

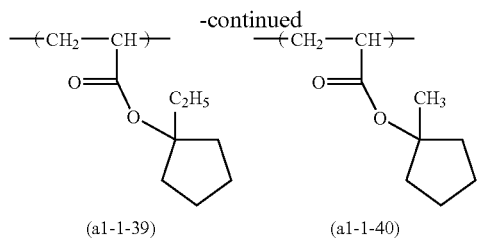
(a1-1-39)  (a1-1-40)
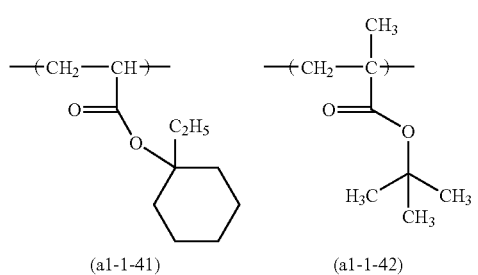
(a1-1-41)  (a1-1-42)
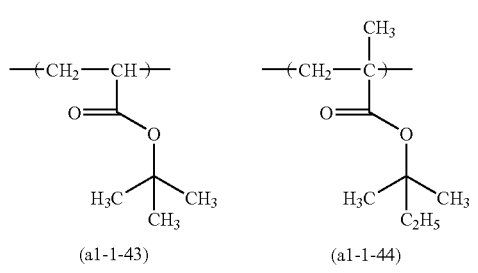
(a1-1-43)  (a1-1-44)
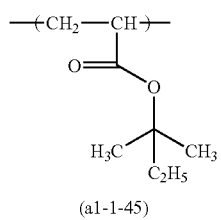
(a1-1-45)
[Chemical Formula 24.]
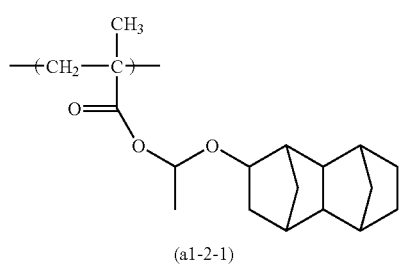
(a1-2-1)
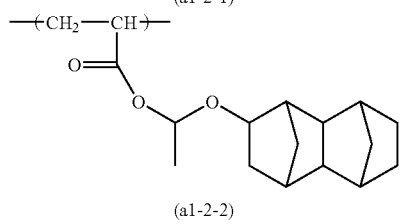
(a1-2-2)
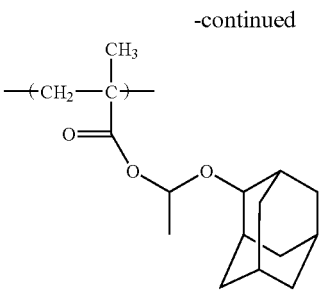
(a1-2-3)
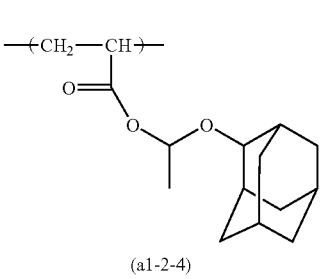
(a1-2-4)
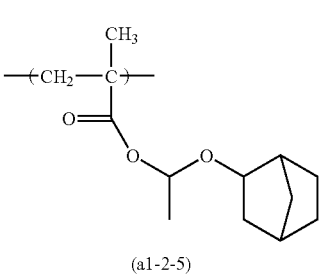
(a1-2-5)
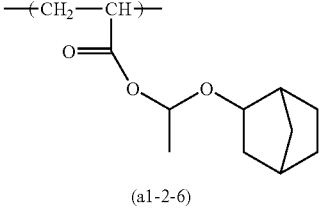
(a1-2-6)
[Chemical Formula 25.]
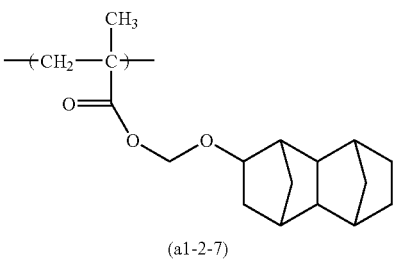
(a1-2-7)
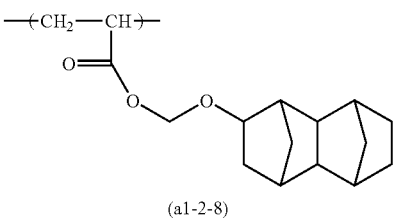
(a1-2-8)

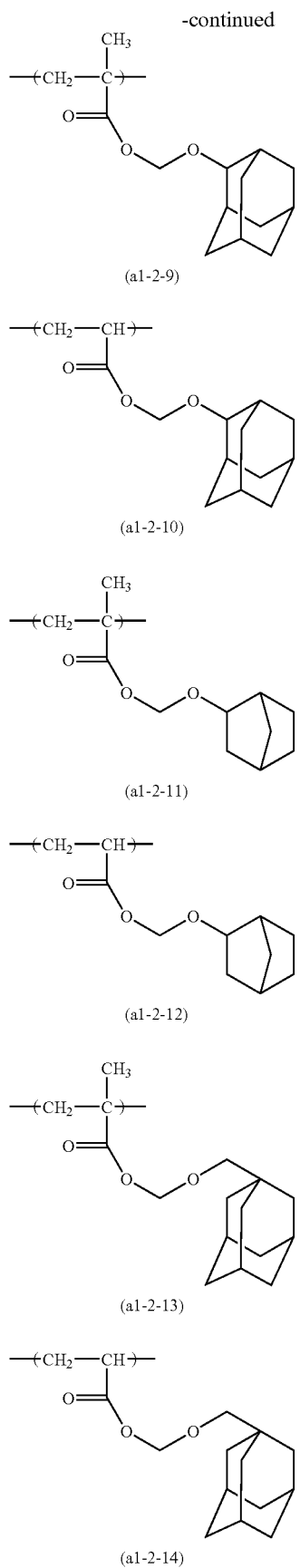
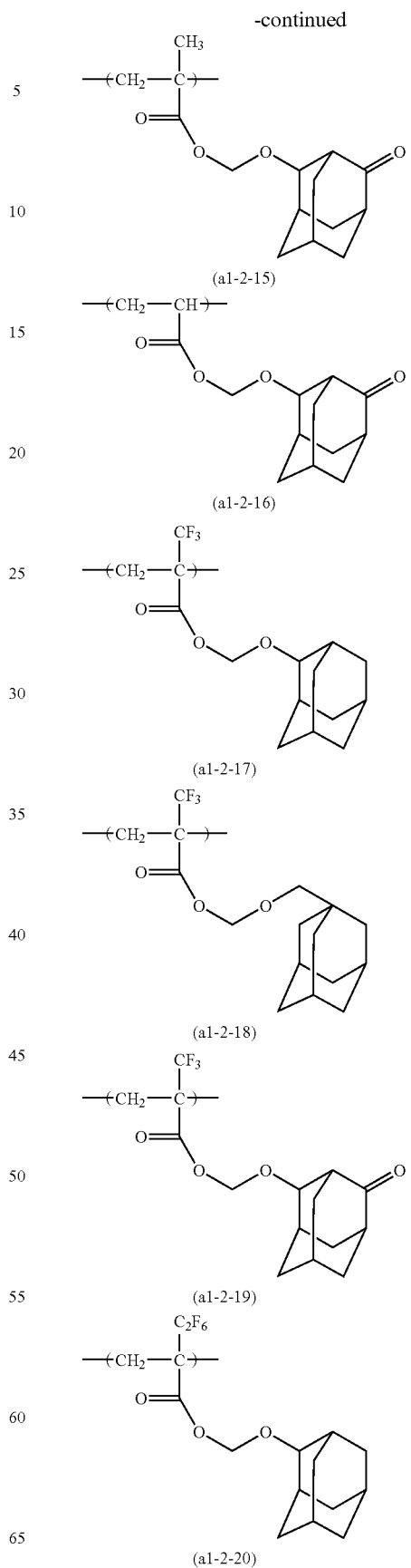

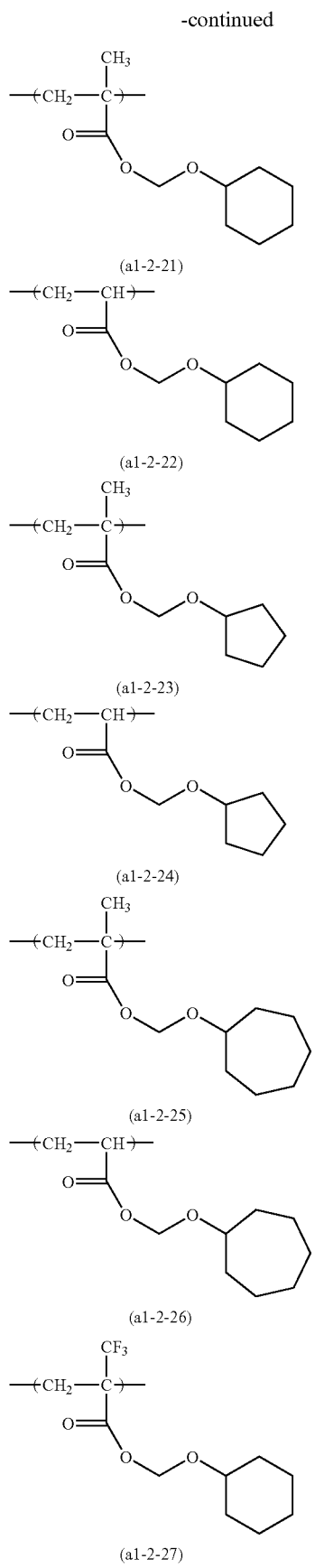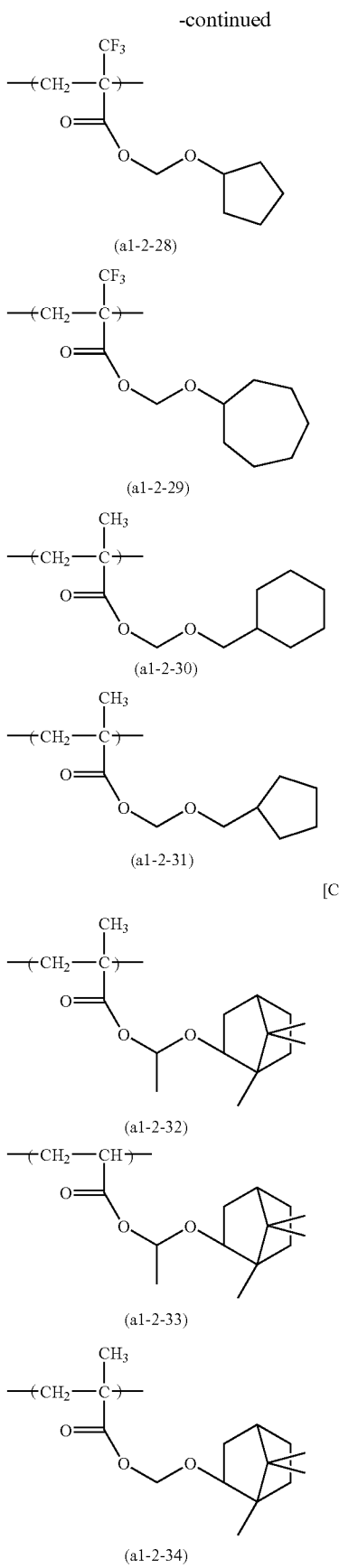

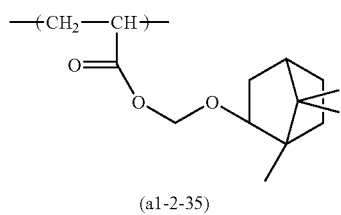
(a1-2-35)
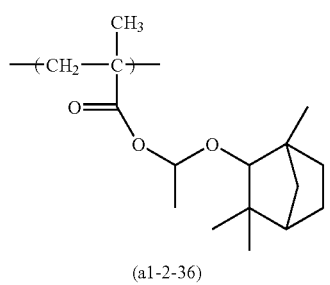
(a1-2-36)
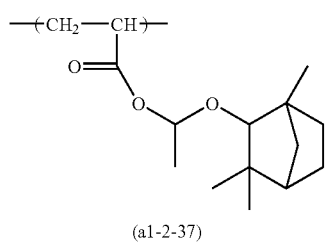
(a1-2-37)
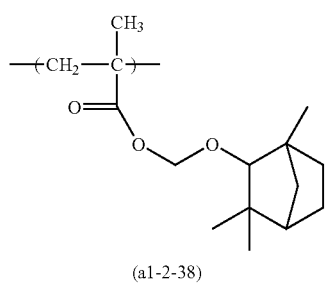
(a1-2-38)
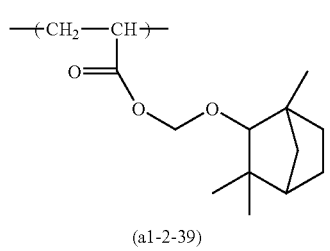
(a1-2-39)
[Chemical Formula 28.]
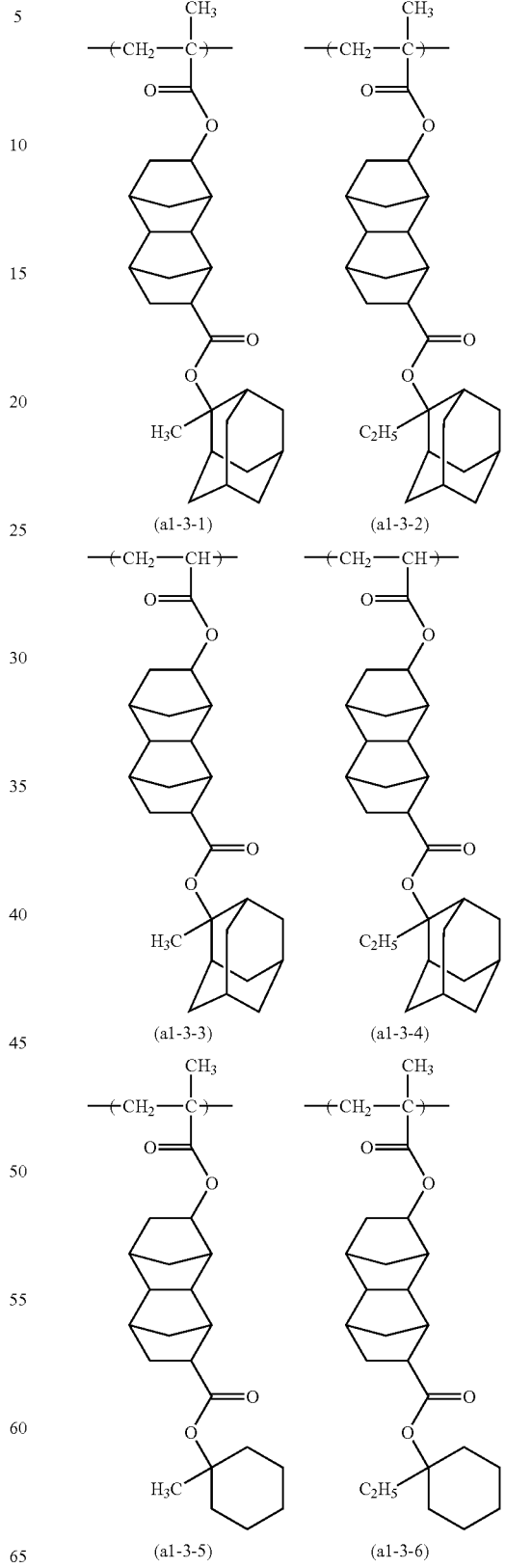
(a1-3-1) (a1-3-2)
(a1-3-3) (a1-3-4)
(a1-3-5) (a1-3-6)

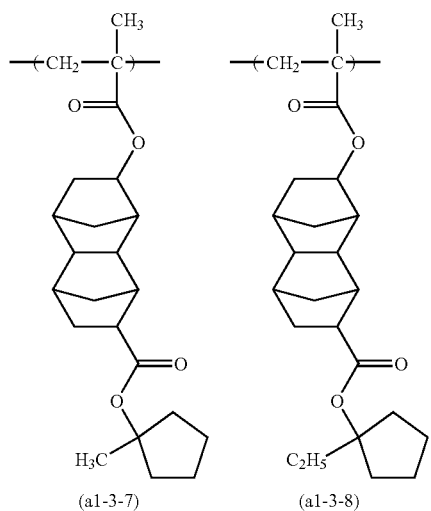
(a1-3-7)  (a1-3-8)
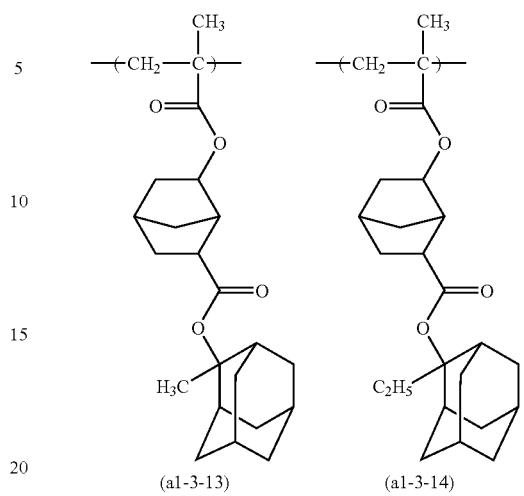
(a1-3-13)  (a1-3-14)
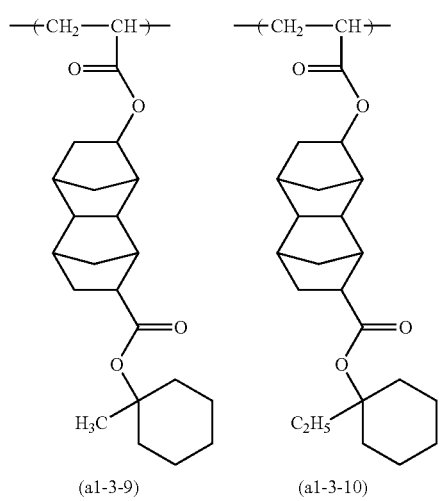
(a1-3-9)  (a1-3-10)
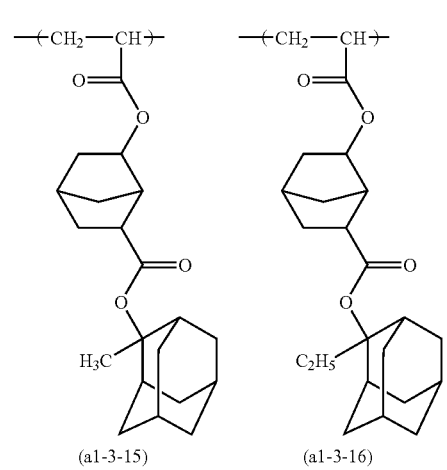
(a1-3-15)  (a1-3-16)
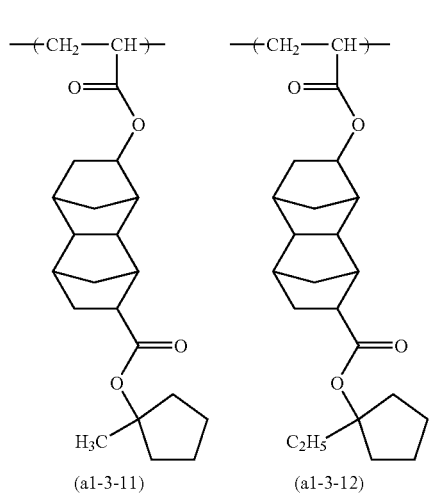
(a1-3-11)  (a1-3-12)
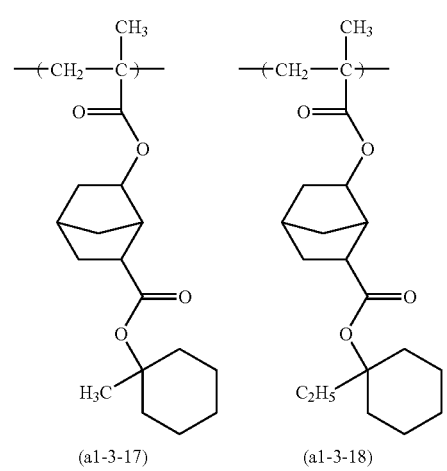
(a1-3-17)  (a1-3-18)

-continued
[Chemical Formula 29.]
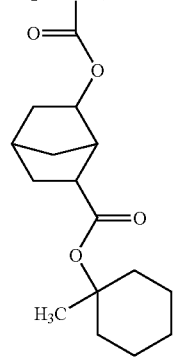
(a1-3-19)
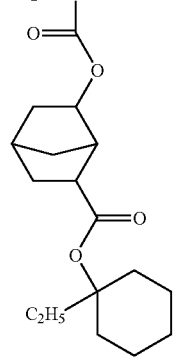
(a1-3-20)
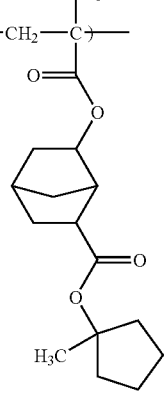
(a1-3-21)
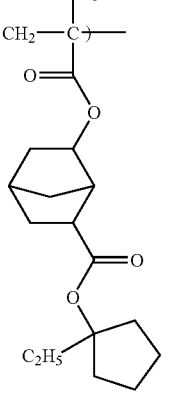
(a1-3-22)
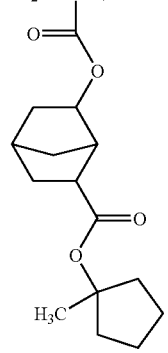
(a1-3-23)
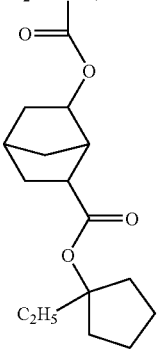
(a1-3-24)
-continued
[Chemical Formula 30.]
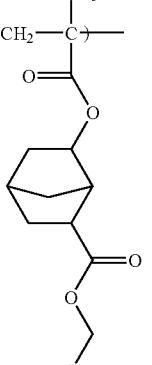
(a1-4-1)
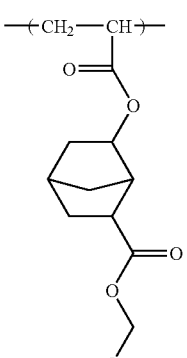
(a1-4-2)
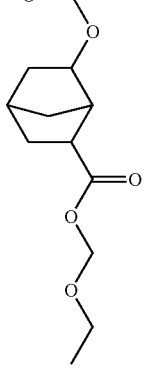
(a1-4-3)
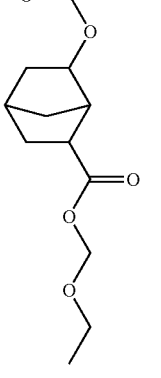
(a1-4-4)
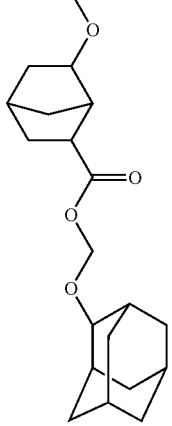
(a1-4-5)
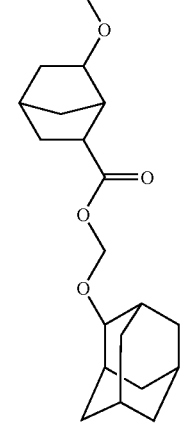
(a1-4-6)

-continued (a1-4-7) (a1-4-8) (a1-4-13) (a1-4-14)

(a1-4-9) (a1-4-10)

(a1-4-11) (a1-4-12) (a1-4-15) (a1-4-16)

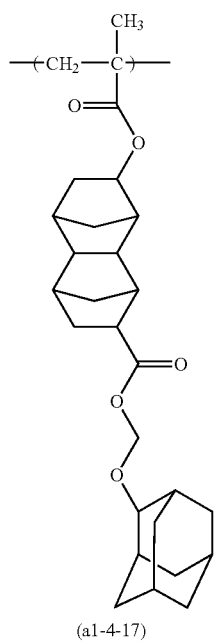
(a1-4-17)
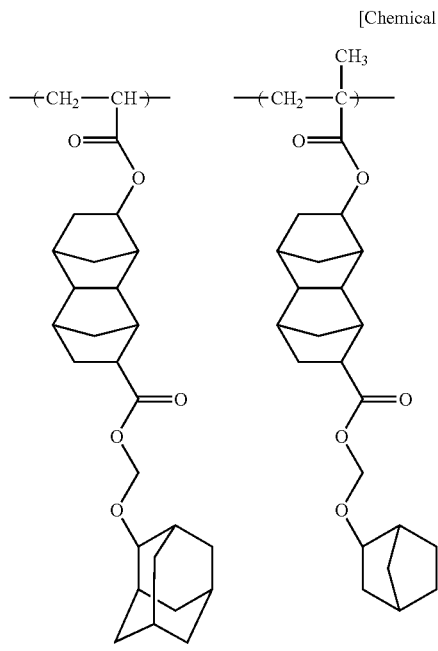
(a1-4-18) (a1-4-19)
[Chemical Formula 31.]
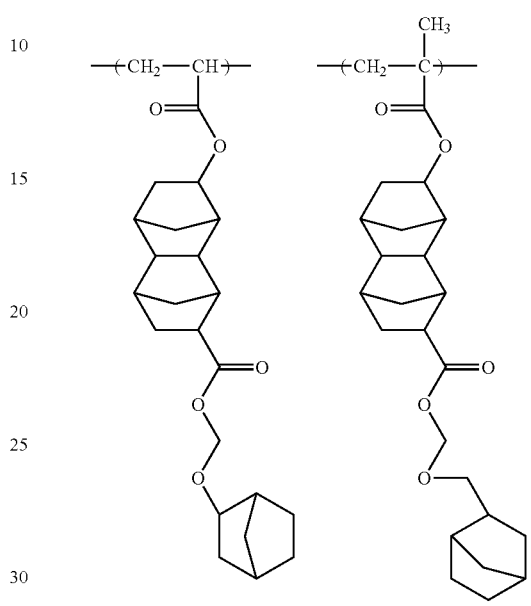
(a1-4-20) (a1-4-21)
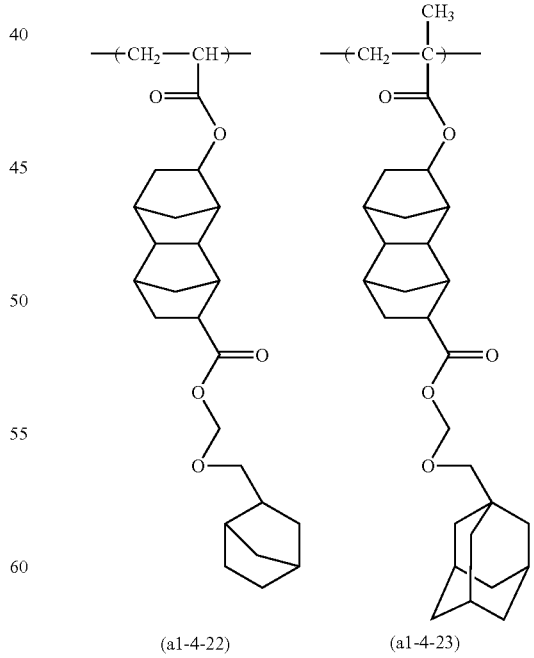
(a1-4-22) (a1-4-23)

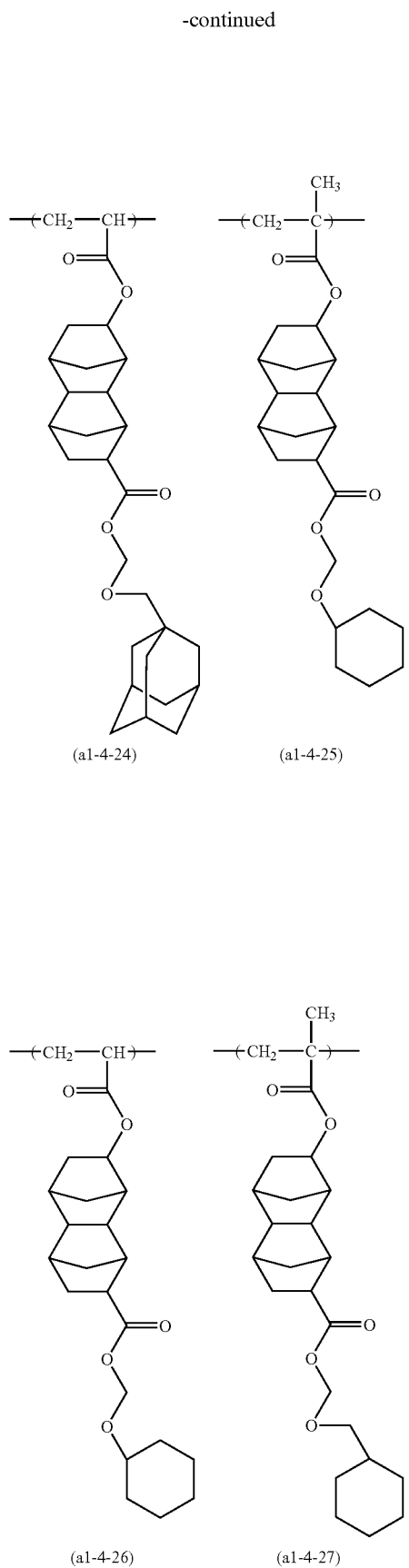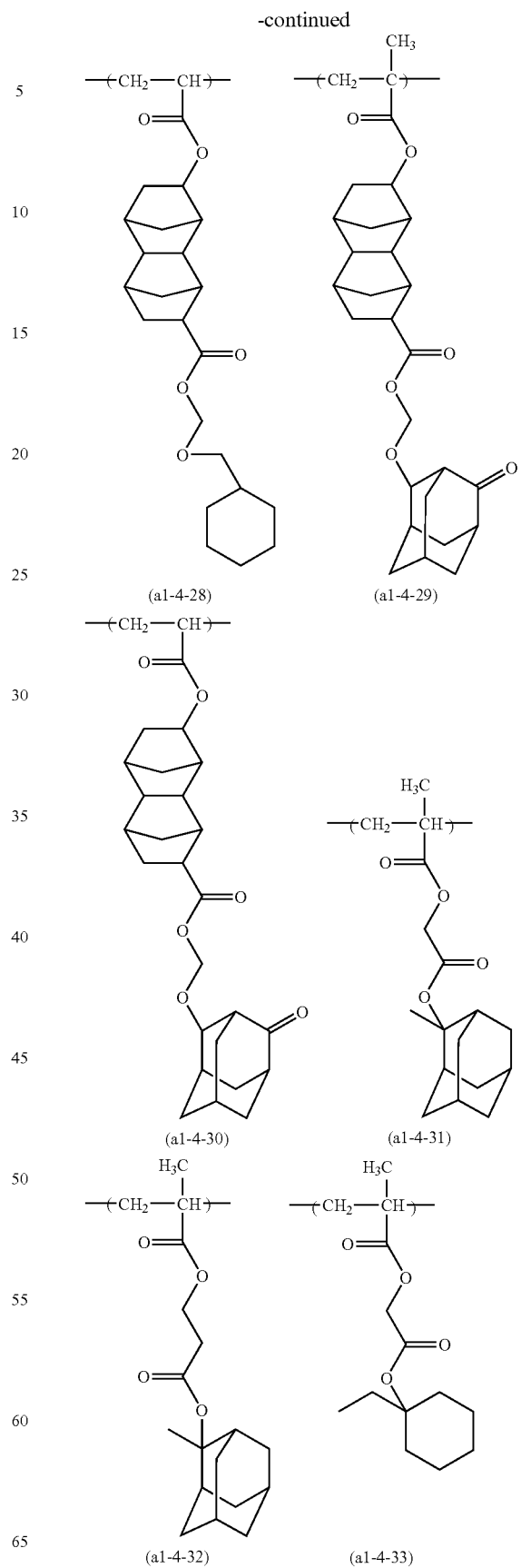

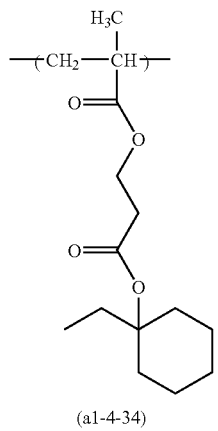 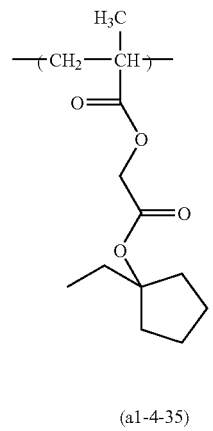

(a1-4-34)     (a1-4-35)

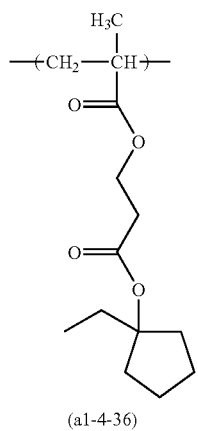 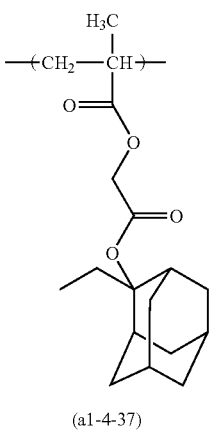

(a1-4-36)     (a1-4-37)

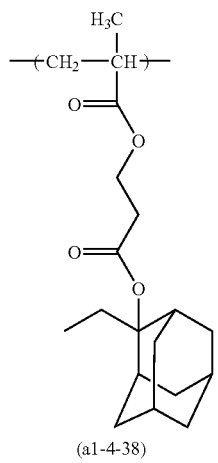 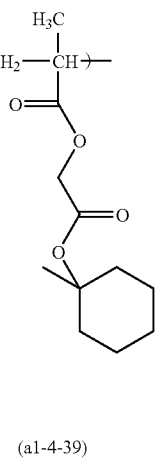

(a1-4-38)     (a1-4-39)

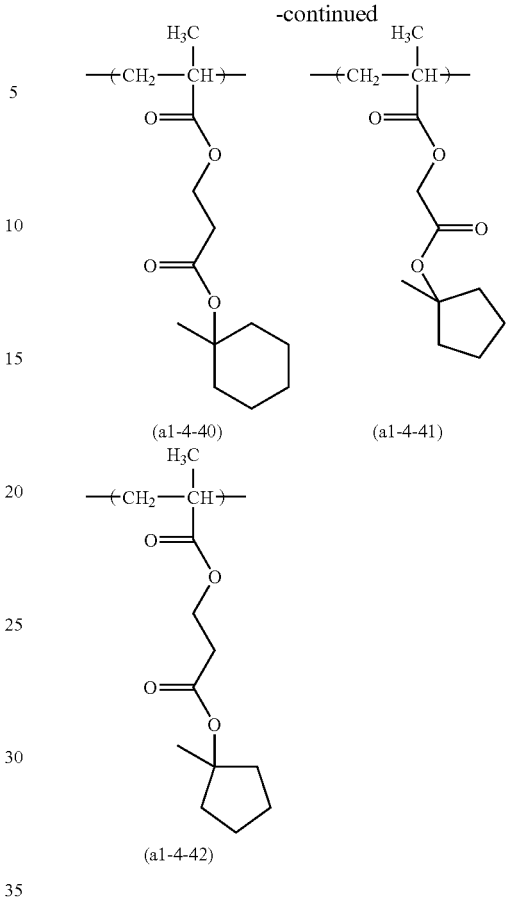

(a1-4-40)     (a1-4-41)

(a1-4-42)

As the structural unit (a1), one type may be used alone, or two or more types may be used in combination.

Among these, structural units represented by general formula (a1-1) are preferable. More specifically, at least one structural unit selected from the group consisting of structural units represented by formulas (a1-1-1) to (a-1-6) and (a1-1-35) to (a1-1-41) is more preferable.

Further, as the structural unit (a1), structural units represented by general formula (a1-1-01) shown below which includes the structural units represented by formulas (a1-1-1) to (a1-1-4), and structural units represented by general formula (a1-1-02) shown below which includes the structural units represented by formulas (a1-1-35) to (a1-1-41) are also preferable.

[Chemical Formula 32.]

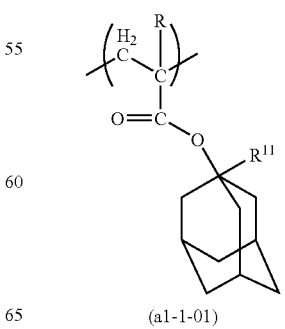

(a1-1-01)

wherein R represents a hydrogen atom, a lower alkyl group or a halogenated lower alkyl group; and $R^{11}$ represents a lower alkyl group.

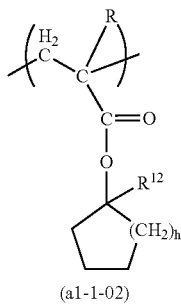

(a1-1-02)

wherein R represents a hydrogen atom, a lower alkyl group or a halogenated lower alkyl group; $R^{12}$ represents a lower alkyl group; and h represents an integer of 1 to 3.

In general formula (a1-1-01), R is as defined above. The lower alkyl group for $R^{11}$ is the same as the lower alkyl group for R above, and is preferably a methyl group or an ethyl group.

In general formula (a1-1-02), R is as defined above. The lower alkyl group for $R^{12}$ is the same as the lower alkyl group for R above. $R^{12}$ is preferably a methyl group or an ethyl group, and most preferably an ethyl group. h is preferably 1 or 2, and most preferably 2.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a positive resist composition prepared from the component (A1). On the other hand, by making the amount of the structural unit (a1) no more than the upper limit of the above-mentioned range, a good balance can be achieved with the other structural units.

-Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the affinity for the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

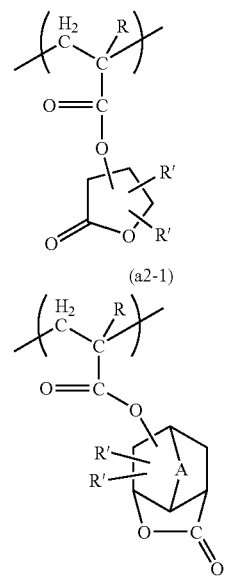

(a2-1)

(a2-2)

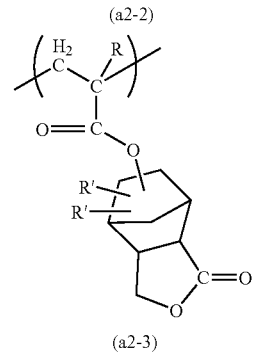

(a2-3)

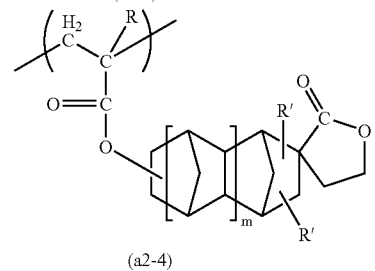

(a2-4)

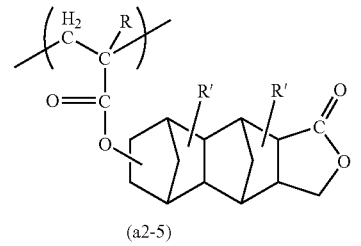

(a2-5)

wherein R represents a hydrogen atom, a lower alkyl group or a halogenated lower alkyl group; R' represents a hydrogen atom, a lower alkyl group or an alkoxy group of 1 to 5 carbon atoms; m represents 0 or 1; and A represents an alkylene group of 1 to 5 carbon atoms or an oxygen atom.

In general formulas (a2-1) to (a2-5), R is the same as R in the structural unit (a1).

The lower alkyl group for R' is the same as the lower alkyl group for R in the structural unit (a1).

Specific examples of alkylene groups of 1 to 5 carbon atoms for A include a methylene group, ethylene group, n-propylene group and isopropylene group.

In the structural units represented by general formulas (a2-1) to (a2-5), in consideration of industrial availability, R' is preferably a hydrogen atom.

Specific examples of structural units represented by general formulas (a2-1) to (a2-5) above are shown below.

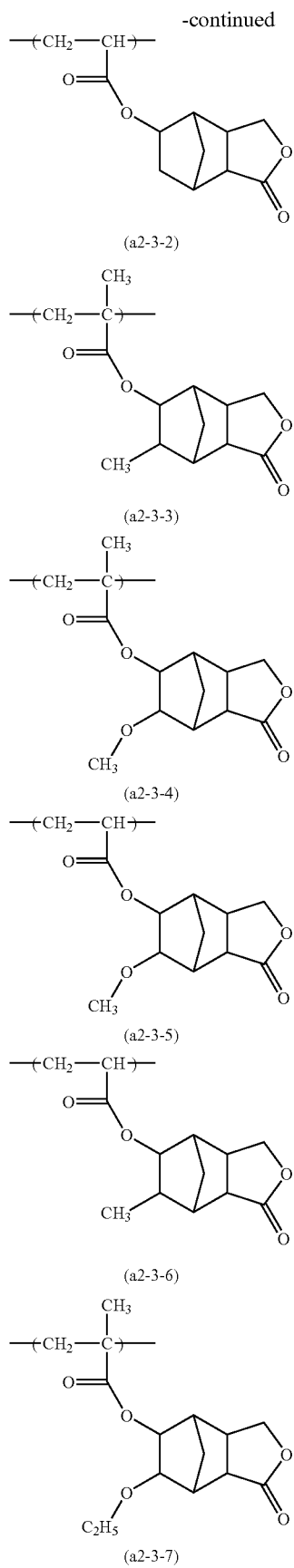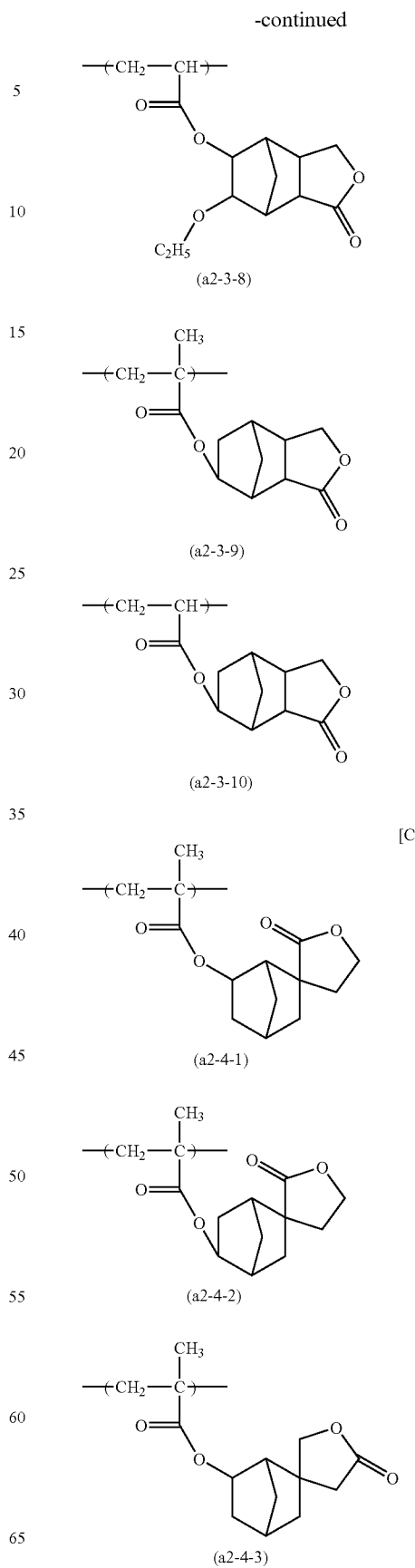

-continued
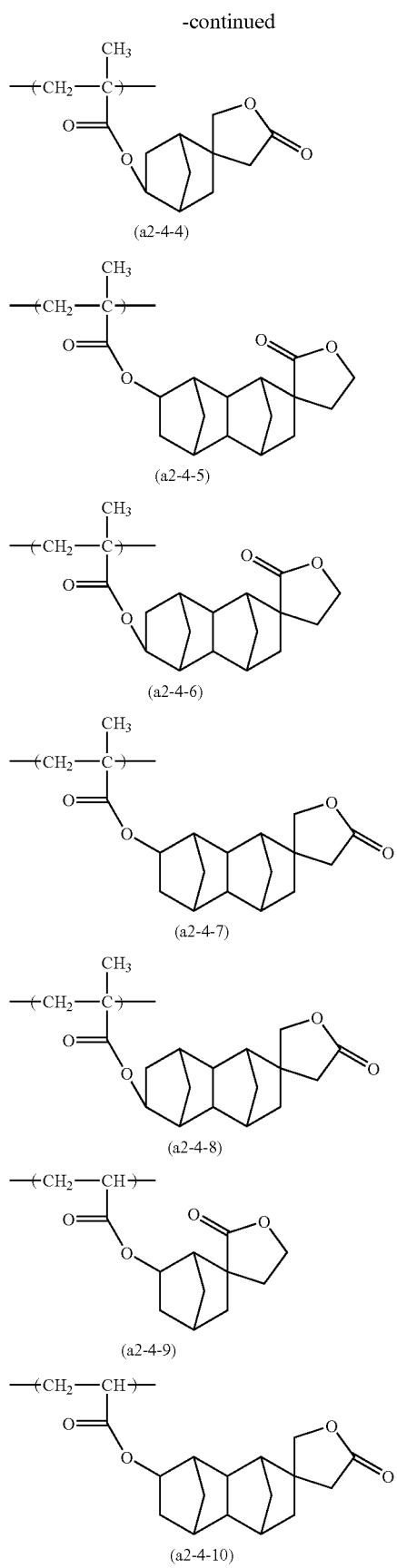
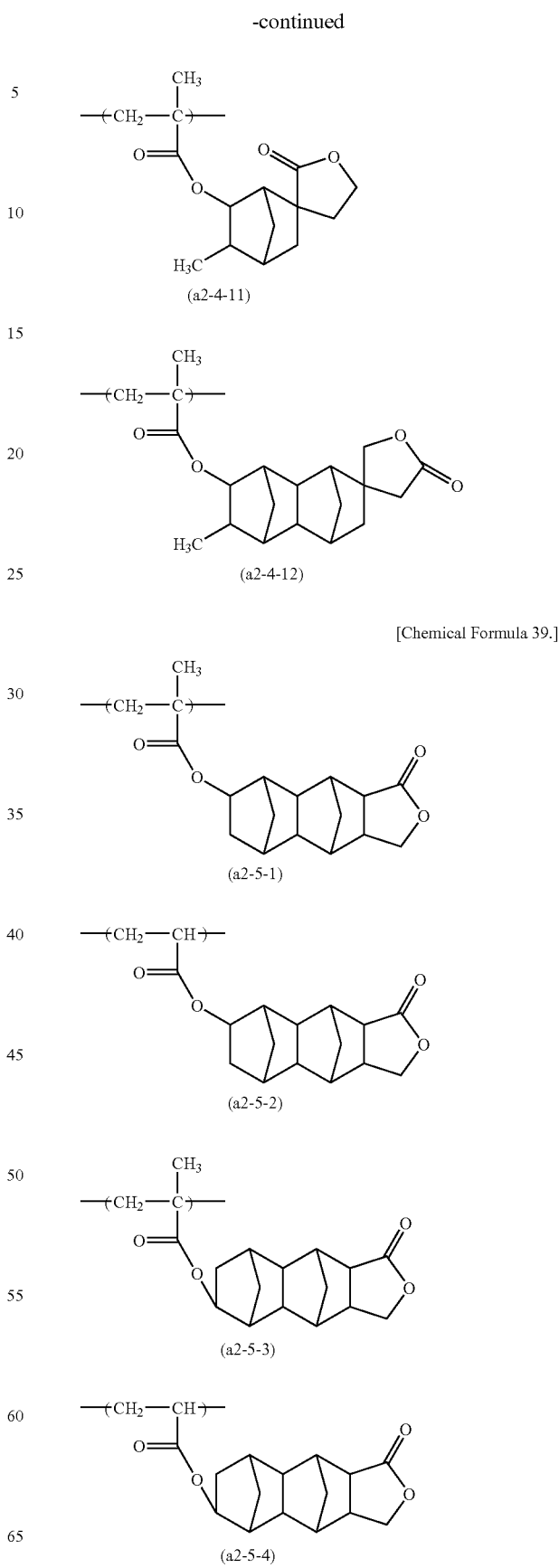
[Chemical Formula 39.]

-continued

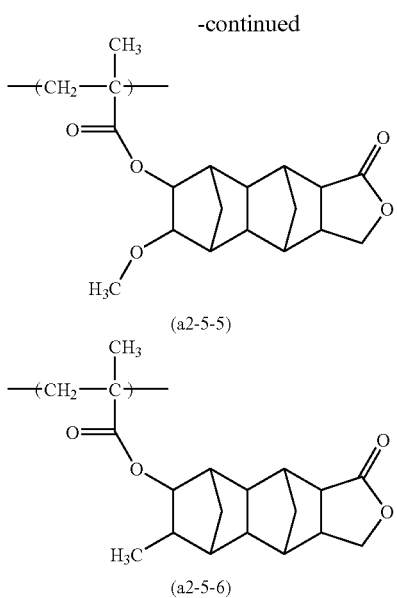

(a2-5-5)

(a2-5-6)

Of these, at least one structural unit selected from the group consisting of formulas (a2-1) to (a2-5) is preferable, and at least one structural unit selected from the group consisting of formulas (a2-1) to (a2-3) is more preferable. Specifically, it is preferable to use at least one structural unit selected from the group consisting of formulas (a2-1-1), (a2-1-2), (a2-2-1), (a2-2-2), (a2-3-1), (a2-3-2), (a2-3-9) and (a2-3-10).

In the component (A1), as the structural unit (a2), one type of structural unit may be used, or two or more types may be used in combination.

In the component (A1), the amount of the structural unit (a2) based on the combined total of all structural units constituting the component (A1) is preferably 5 to 60 mol %, more preferably 10 to 50 mol %, and still more preferably 20 to 50 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

-Structural Unit (a3)

The structural unit (a3) is a structural unit derived from an acrylate ester having a polar group-containing aliphatic hydrocarbon group. When the component (A1) includes the structural unit (a3), the hydrophilicity of the component (A1) is improved, and hence, the affinity of the component (A1) for the developing solution is improved. As a result, the solubility of the exposed portions in an alkali developing solution improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), and (a3-3) shown below are preferable.

[Chemical Formula 40.]

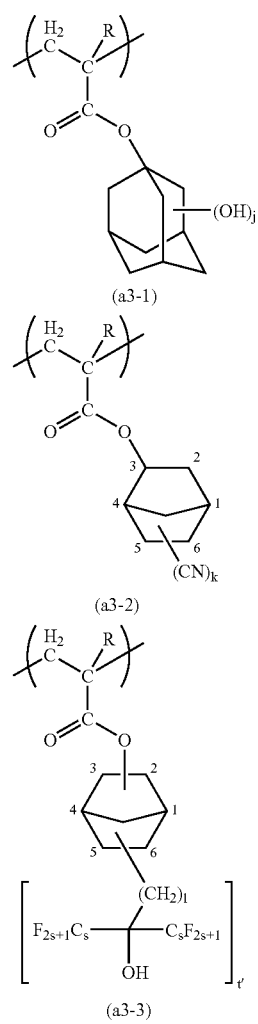

(a3-1)

(a3-2)

(a3-3)

wherein R is as defined above; j is an integer of 1 to 3; k is an integer of 1 to 3; t' is an integer of 1 to 3; 1 is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

In formula (a3-2), k is preferably 1. The cyano group is preferably bonded to the 5th or 6th position of the norbonyl group.

In formula (a3-3), t' is preferably 1, 1 is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbonyl group.

In the component (A1), as the structural unit (a3), one type of structural unit may be used, or two or more types may be used in combination.

When the component (A1) contains the structural unit (a3), the amount of structural unit (a3) based on the combined total of all structural units constituting the component (A1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

-Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 41.]

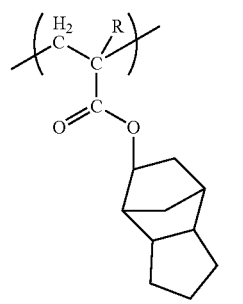

(a4-1)

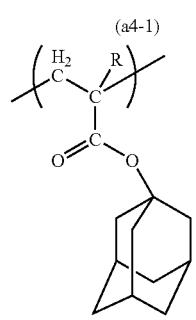

(a4-2)

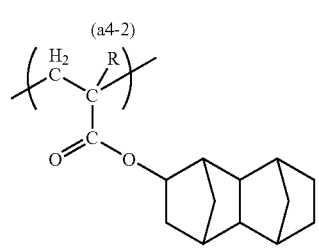

(a4-3)

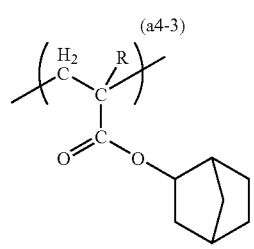

(a4-4)

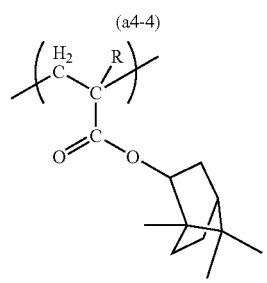

(a4-5)

wherein R is as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the present invention, the component (A1) is a resin component (polymer) which exhibits increased solubility in an alkali developing solution under action of acid. As such a resin component (polymer), a copolymer having the structural units (a1), (a2) and (a3) can be preferably used. Examples of such a copolymer include a copolymer consisting of the structural units (a1) and (a2) and (a3), and a copolymer consisting of the structural units (a1), (a2), (a3) and (a4).

As the component (A1), one type may be used, or two or more types may be used in combination.

In the present invention, as the component (A1), copolymers (A1-1) to (A 1-3) respectively including combinations of structural units represented by general formulas (A1-1) to (A1-3) shown below are preferable.

[Chemical Formula 42.]

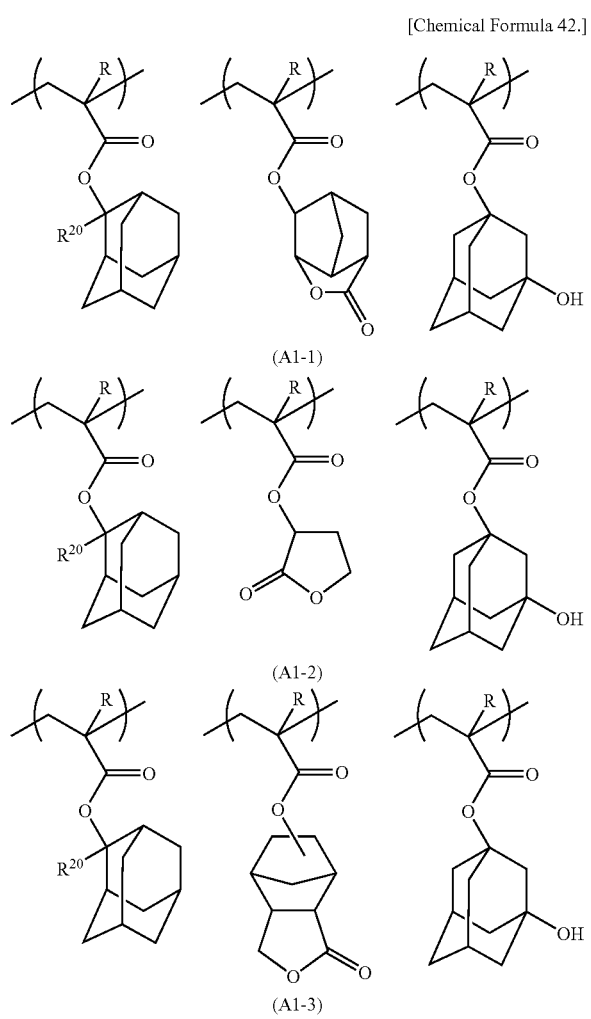

wherein R is as defined above, wherein the plurality of R may be the same or different; and $R^{20}$ represents a lower alkyl group.

In general formulas (A1-1) to (A1-3), R is as defined above, and is preferably a hydrogen atom or a methyl group.

In general formulas (A1-1) to (A1-3), $R^{20}$ represents a lower alkyl group, and is preferably a methyl group or ethyl group.

In the component (A1), as the copolymers (A1-1) to (A1-3), one type of copolymer may be used, or two or more types may be used in combination.

When two or more types of the copolymers (A1-1) to (A1-3) are used in combination, a combination of the copolymer (A1-2) and the copolymer (A1-3) may be exemplified as a preferable combination.

In the component (A1), the content of the copolymers (A1-1) to (A 1-3) is preferably 70% by weight or more, more preferably 80% by weight or more, and may be even 100% by weight. It is particularly desirable that the content of the copolymer (A1-1) or (A1-2) be 100% by weight. By making the content at least as large as the lower limit of the above-mentioned range, the lithography properties as a positive resist composition are improved.

The component (A1) can be obtained, for example, by a conventional radical polymerization or the like of the monomers corresponding with each of the structural units, using an azo-type radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, still more preferably 4,000 to 20,000, and most preferably 5,000 to 20,000. When the weight average molecular weight is within the above-mentioned range, the component (A1) exhibits satisfactory solubility in a resist solvent when used as a resist, and dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

Further, as the component (A1), an alkali-soluble resin component other than the copolymers (A1-1) to (A1-3), such as other polymeric compounds used in conventional resist compositions may be used.

In the positive resist composition of the present invention, the amount of the component (A1) can be appropriately adjusted depending on the thickness of the resist film to be formed, and the like.

<Component (B)>

In the resist composition of the present invention, the component (B) contains an acid generator (B1) (hereafter, referred to as "component (B1)") consisting of a compound represented by general formula (b1-14) shown above.

In general formula (b1-14), as $R^{7\prime\prime\prime}$ to $R^{9\prime\prime\prime}$ and $X^-$, the same as those described above in connection with the compound of the third aspect of the present invention can be exemplified.

As the component (B) contains the component (B1), the mask reproducibility of a resist pattern formed is improved. More specifically, for example, when a contact and hole (C/H) pattern is formed, the circularity of the holes and the uniformity (CDU) of the diameter (CD) is improved. Further, lithography properties such as mask error factor (MEF) and removability (ability to allow substantially equivalent holes to be formed) of the C/H pattern formed are improved. Also, when a line and space resist pattern (L/S pattern) is formed, lithography property such as MEF is improved.

In addition, the resist composition of the present invention can be preferably used as a resist composition for immersion exposure in a method of forming a resist pattern including immersion exposure, and excellent lithography properties can be achieved. Further, the resist composition of the present invention can be preferably used as a resist composition for forming an upper-layer resist film in a method of forming a resist pattern including formation of a triple-layer resist laminate, and excellent lithography properties can be achieved.

As the anion moiety of the component (B1), it is preferable to use an anion represented by general formula "$R^{14}SO_3^-$" or "$R^1$—O—$Y^1$—$SO_3^-$" shown above or an anion represented by general formula (b-3) or (b-4) shown above, and it is more preferable to use an anion represented by general formula "$R^{14}SO_3^-$" or "$R^1$—O—$Y^1$—$SO_3^-$" shown above.

As the component (B), one type of acid generator may be used, or two or more types may be used in combination.

In the resist composition of the present invention, the amount of the component (B1) based on the combined total of the component (B) is preferably 40% by weight or more, more preferably 60% by weight or more, and may be even 100% by weight. By making the amount of the component (B1) at least as large as the lower limit of the above-mentioned range, the shape of the resist pattern becomes satisfactory. Especially, when the component (B1) is used in a resist composition for immersion exposure or a resist composition for forming an upper-layer resist film, the lithography properties of the formed patterns are improved. Further, when the resist composition is used for forming an upper-layer resist film, the resist composition is advantageous in that the matching of the resist with the lower-layer film becomes satisfactory in the formation of a triple-layer resist laminate, and hence, footing of the resist pattern and the like can be suppressed.

Furthermore, in the resist composition of the present invention, the amount of the component (B1) is preferably 1 to 30 parts by weight, more preferably 3 to 18 parts by weight, most preferably 5 to 16 parts by weight, relative to 100 parts by weight of the component (A). By making the amount of the component (B1) at least as large as the lower limit of the above-mentioned range, the lithography properties of the formed resist pattern can be improved, especially when it is used in a resist composition for immersion exposure or a resist composition for forming an upper-layer resist film. On the other hand, by making the amount of the component (B1) no more than the upper limit of the above-mentioned range, the storage stability becomes satisfactory.

In the component (B), an acid generator (B2) other than the aforementioned component (B1) (hereafter, referred to as "component (B2)") may be used in combination with the component (B1).

As the component (B2), there is no particular limitation as long as it is an acid generator other than the component (B1), and any of the known acid generators used in conventional chemically amplified resist compositions can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator, a compound represented by general formula (b-1) or (b-2) shown below can be used.

[Chemical Formula 43.]

$$R^{2\prime\prime}\!-\!\underset{\underset{R^{3\prime\prime}}{|}}{\overset{\overset{R^{1\prime\prime}}{|}}{S^+}}\;\;R^{4\prime\prime}SO_3^- \qquad \underset{R^{6\prime\prime}}{\overset{R^{5\prime\prime}}{\diagdown}}I^+\;\;R^{4\prime\prime}SO_3^-$$

(b-1)        (b-2)

wherein $R^{1\prime\prime}$ to $R^{3\prime\prime}$, $R^{5\prime\prime}$ and $R^{6\prime\prime}$ each independently represents an aryl group or alkyl group, wherein two of $R^{1\prime\prime}$ to $R^{3\prime\prime}$ in formula (b-1) may be bonded to each other to form a ring with the sulfur atom; and $R^{4\prime\prime}$ represents a linear, branched or cyclic alkyl group or fluorinated alkyl group, with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ are the same as $R^{7\prime\prime}$ to $R^{9\prime\prime}$ in formula (b1-14) above, except that the alkoxyalkyloxy group or the alkoxycarbonylalkyloxy group is not a substituent for substituting hydrogen atom(s).

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

It is particularly desirable that each of $R^{1\prime\prime}$ to $R^{3\prime\prime}$ is a phenyl group or a naphthyl group.

$R^{4\prime\prime}$ represents a linear, branched or cyclic alkyl or fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group, as described for $R^{1\prime\prime}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (percentage of fluorine atoms within the alkyl group) is preferably from 10 to 100%, more preferably from 50 to 100%, and it is particularly desirable that all hydrogen atoms are substituted with fluorine atoms because the acid strength increases.

$R^{4\prime\prime}$ is most preferably a linear or cyclic alkyl group or fluorinated alkyl group.

In formula (b-2), $R^{5\prime\prime}$ and $R^{6\prime\prime}$ each independently represents an aryl group or alkyl group. At least one of $R^{5\prime\prime}$ and $R^{6\prime\prime}$ represents an aryl group. It is preferable that both of $R^{5\prime\prime}$ and $R^{6\prime\prime}$ represent an aryl group.

As the aryl group for $R^{5\prime\prime}$ and $R^{6\prime\prime}$, the same as the aryl groups for $R^{1\prime\prime}$ to $R^{3\prime\prime}$ can be exemplified.

As the alkyl group for $R^{5\prime\prime}$ and $R^{6\prime\prime}$, the same as the alkyl groups for $R^{1\prime\prime}$ to $R^{3\prime\prime}$ can be exemplified.

It is particularly desirable that both of $R^{5\prime\prime}$ and $R^{6\prime\prime}$ represents a phenyl group.

As $R^{4\prime\prime}$ in formula (b-2), the same as those mentioned above for $R^{4\prime\prime}$ in formula (b-1) can be exemplified.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3, 5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate. It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown above (the cation moiety is the same as (b-1) or (b-2)) may be used.

Furthermore, as an onium salt-based acid generator, a sulfonium salt having a cation moiety represented by general formula (b-5) or (b-6) shown below may be used.

[Chemical Formula 44.]

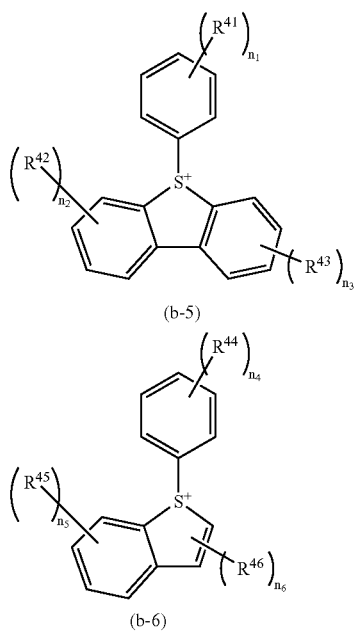

(b-5)

(b-6)

wherein $R^{41}$ to $R^{46}$ each independently represents an alkyl group, an acetyl group, an alkoxy group, a carboxy group, a hydroxyl group or a hydroxyalkyl group; $n_1$ to $n_5$ each independently represents an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, hydroxyethyl group and hydroxypropyl group.

When the subscripts $n_1$ to $n_6$ of $R^{41}$ to $R^{46}$ represent an integer of 2 or more, the plurality of $R^{41}$ to $R^{46}$ may be the same or different.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

n6 is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties ($R^{4'''}SO_3^-$) for onium salt-based acid generators represented by general formula (b-1) or (b-2) shown above; and anion moieties represented by general formula (b-3) or (b-4) shown above. Among these, fluorinated alkylsulfonic acid ions are preferable, more preferably fluorinated alkylsulfonic acid ions of 1 to 4 carbon atoms, and linear perfluoroalkylsulfonic acid ions of 1 to 4 carbon atoms are particularly desirable. Specific examples include a trifluoromethylsulfonic acid ion, heptafluoro-n-propylsulfonic ion and nonafluoro-n-butylsulfonic acid ion.

In the present description, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

[Chemical Formula 45.]

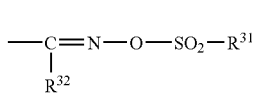

(B-1)

wherein $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 46.]

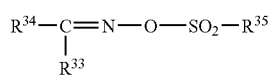

(B-2)

wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 47.]

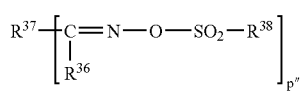

(B-3)

wherein $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(ptoluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be exemplified.

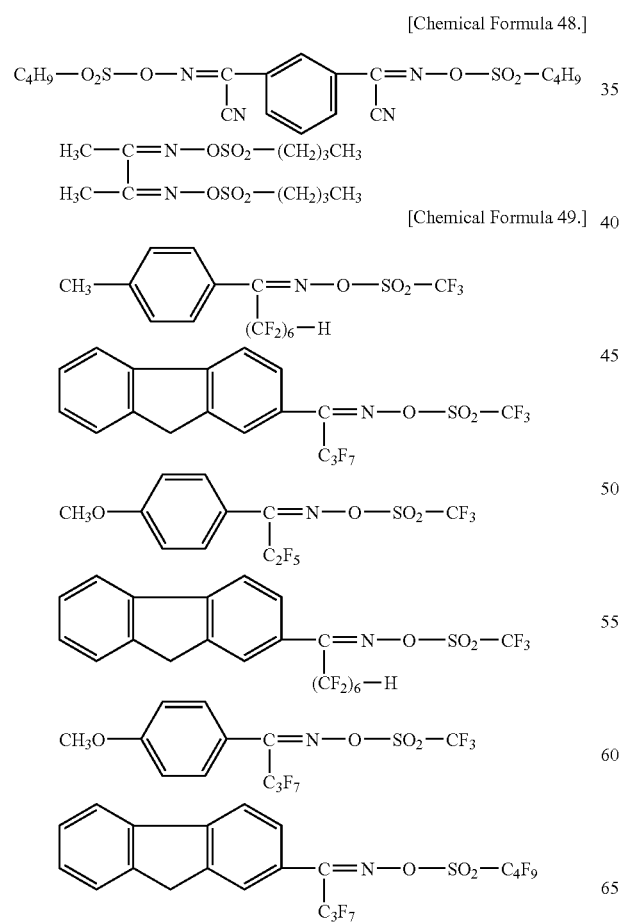

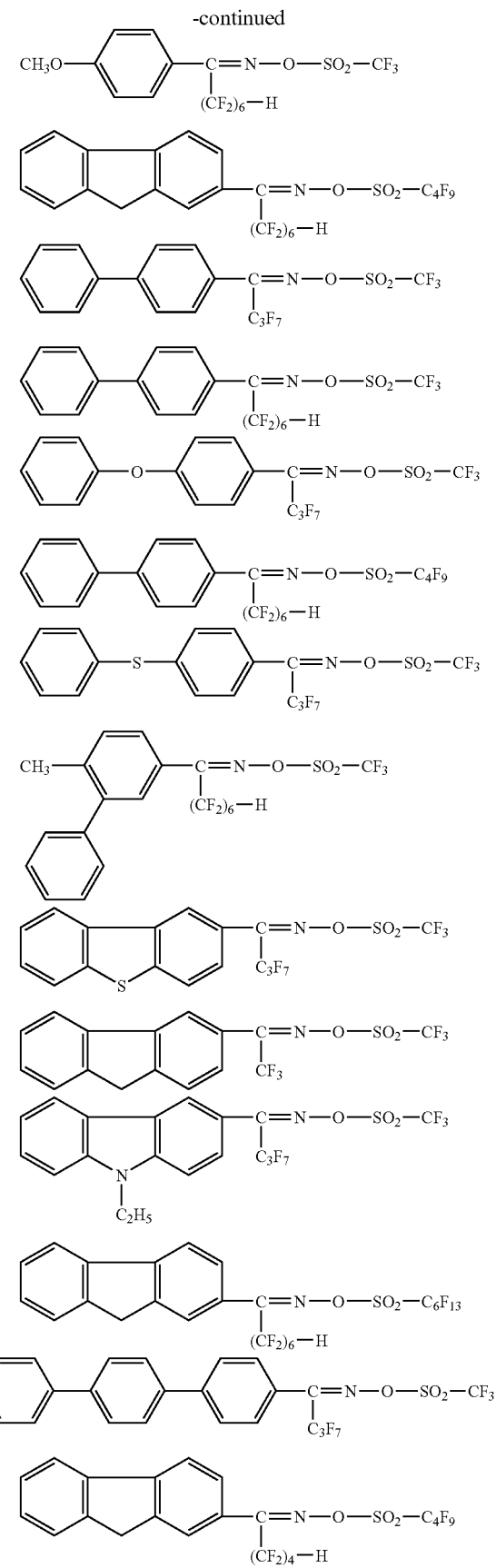

Among the above-exemplified compounds, the following 4 compounds are preferable.

[Chemical Formula 50.]

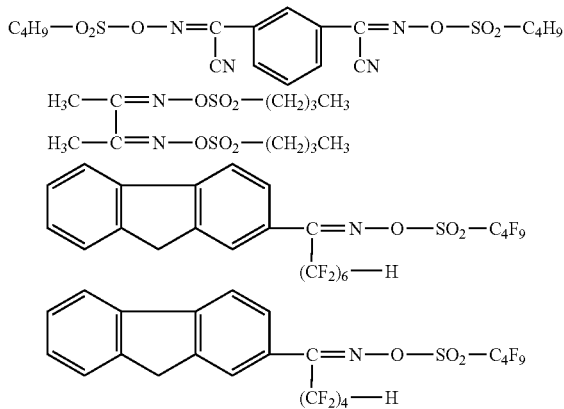

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazometbylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be exemplified.

As the component (B2), one type of acid generator may be used, or two or more types may be used in combination.

The total amount of the component (B) within the resist composition of the present invention is 0.5 to 30 parts by weight, and preferably 1 to 20 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Component (D)>

In the resist composition of the present invention, for improving the resist pattern shape and the post exposure stability of the latent image formed by the pattern-wise exposure of the resist layer, a nitrogen-containing organic compound (D) (hereafter referred to as the component (D)) can be added as an optional component.

A multitude of these components (D) have already been proposed, and any of these known compounds may be used, although an aliphatic amine, and particularly a secondary aliphatic amine or tertiary aliphatic amine is preferable. In the present description and claims, the term "aliphatic" is a relative concept used in relation to the term "aromatic", and defines a group or compound that has no aromaticity.

The term "aliphatic cyclic group" refers to a monocyclic group or polycyclic group that has no aromaticity. An aliphatic amine is an amine having one or more aliphatic groups, and the aliphatic groups preferably have 1 to 12 carbon atoms.

Examples of these aliphatic amines include amines in which at least one hydrogen atom of ammonia ($NII_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, tri-n-pentylamine and tri-n-octylamine are more preferable, and tri-n-pentylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazahicyclo[2.2.2]octane.

These compounds can be used either alone, or in combinations of two or more different compounds.

The component (D) is typically used in an amount within a range from 0.01 to 5.0 parts by weight, relative to 100 parts by weight of the component (A).

<Optional Component> [Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

<Component (S)>

The resist composition according to the first aspect of the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME), ethyl lactate (EL) and γ-butyrolactone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, as the component (S), a mixed solvent of a mixture of PGMEA and PGME with γ-butyrolactone is also preferable. The mixing ratio (former: latter) of such a mixed solvent is preferably from 99.9:0.1 to 80:20, more preferably from 99.9:0.1 to 90:10, and most preferably from 99:9:0.1 to 95:5.

By virtue of the above-mentioned range, the rectangularity of the resist pattern is improved.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 5 to 15% by weight.

In the present invention, an acid generator (B1) consisting of a compound represented by general formula (b1-14) above is used. The component (B1) has a structure in which hydroxyl group(s) bonded to the aryl group is protected with a tertiary alkyl ester-type acid dissociable group(s) or an acetal-type acid dissociable group(s) such as an alkoxyalkyl group, and the structure does not change at unexposed portions. Therefore, it is presumed that the compound represented by general formula (b1-14) above exhibits the effect of inhibiting dissolution of the component (A1) in an alkali developing solution at unexposed portions of a resist film.

On the other hand, at exposed portions, during post exposure bake (PEB), the acid dissociable group(s) is dissociated from the oxygen atom constituting the hydroxyl group by generated acid, and a compound in which a hydroxyl group is bonded to the aryl group is generated. As a result, it is presumed that the compound represented by general formula (b1-14) above exhibits the effect of promoting dissolution of the component (A1) in an alkali developing solution.

Therefore, it is presumed that a high contrast between exposed portions and unexposed portions can be achieved.

For the reasons described above, it is presumed that, when the resist composition of the present invention is a positive resist composition, by using a base component in combination with an acid generator (the component (B1)), the mask reproducibility of a resist pattern formed is improved. More specifically, for example, it is presumed that, when a contact and hole (C/H) pattern is formed, the circularity of the holes and the uniformity (CDU) of the diameter (CD) is improved. Further, it is presumed that lithography properties such as mask error factor (MEF) and removability (ability to allow substantially equivalent holes to be formed) of the C/H pattern formed are improved. Also, it is presumed that, when a line and space resist pattern (L/S pattern) is formed, lithography property such as MEF is improved.

In addition, it is presumed that the resist composition of the present invention can be preferably used as a resist composition for immersion exposure in a method of forming a resist pattern including immersion exposure, and excellent lithography properties can be achieved. Further, it is presumed that the resist composition of the present invention can be preferably used as a resist composition for forming an upper-layer resist film in a method of forming a resist pattern including formation of a triple-layer resist laminate, and excellent lithography properties can be achieved.

<<Method of Forming a Resist Pattern>>

Next, the method of forming a resist pattern according to the second aspect of the present invention wilt be described.

The method of forming a resist pattern according to the present invention includes: applying a resist composition of the first aspect of the present invention to a substrate to form a resist film on the substrate; conducting exposure of the resist film; and alkali-developing the resist film to form a resist pattern.

More specifically, the method for forming a resist pattern according to the present invention can be performed, for example, as follows. Firstly, a resist composition according to the first aspect of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the like, the resist film is selectively exposed to an ArF excimer laser beam through a desired mask pattern, followed by post exposure bake (PEB) under temperature conditions of 80 to 150° C. for 40 to 120 seconds, preferably 60 to 90 seconds. Subsequently, developing is conducted using an alkali developing solution such as a 0.1 to 10% by weight aqueous solution of tetramethylammonium hydroxide, preferably followed by rinsing with pure water, and drying. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be exemplified. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-exemplified substrates provided with an inorganic and/or organic film on the surface thereof may be used. As the inorganic film, an inorganic antireflection film (inorganic BARC) can be exemplified. As the organic film, an organic antireflection film (organic BARC) can be exemplified.

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV, and particularly effective to ArF excimer laser. Further, the resist composition of the present invention is also effective to immersion exposure.

EXAMPLES

As follows is a description of examples of the present invention, although the scope of the present invention is by no way limited by these examples.

Synthesis Example 1

Synthesis of Compound (1)

[Chemical Formula 51.]

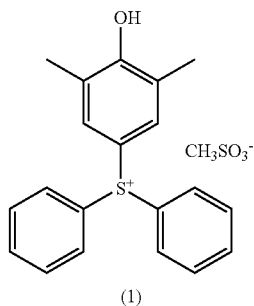

(1)

Phosphorous oxide (8.53 g), 2,6-dimethylphenol (8.81 g) and diphenylsulfoxide (12.2 g) were added in small amounts to methanesulfonic acid (60.75 g) which was controlled to 20° C. or lower. The resultant was matured for 30 minutes while controlling the temperature to 15 to 20° C., followed by elevating the temperature to 40° C. and maturing for 2 hours. Then, the reaction liquid was dropwise added to pure water (109.35 g) which was cooled to 15° C. or lower. Thereafter, dichloromethane (54.68 g) was added thereto and stirred, and the dichloromethane phase was collected. Hexane (386.86 g) at a temperature of 20 to 25° C. was charged into a separate vessel, and the dichloromethane phase was dropwise added thereto. The resultant was matured at 20 to 25° C. for 30 minutes, followed by filtration, thereby obtaining the objective compound (yield: 70.9%).

The obtained compound was analyzed by $^1$H-NMR.

$^1$H-NMR (DMSO-d6, 600MHz): δ(ppm)=7.61-7.72(m, 10H, phenyl), 7.14(S, 2H, H$^c$), 3.12(S, 3H, H$^b$), 2.22(s, 6H, H$^a$).

From the results shown above, it was confirmed that the compound had a structure shown below.

[Chemical Formula 52.]

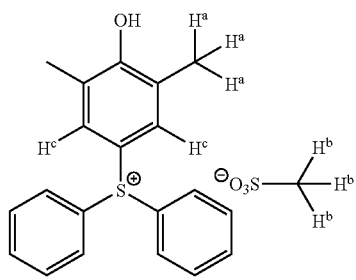

Synthesis Example 2

Synthesis of Compound (2)

[Chemical Formula 53.]

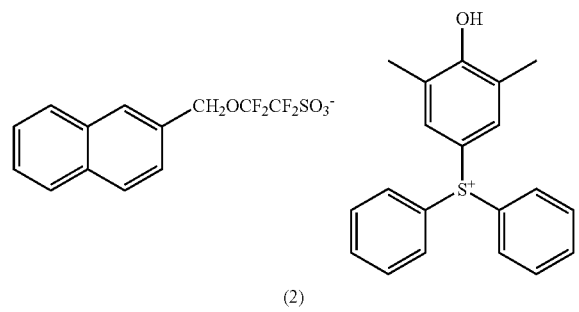

(2)

5.00 g of the compound (1) was dissolved in a mixed solution of 25.00 g of water and 24.03 g of dichloromethane. Then, lithium 2-naphthylmethoxytetrafluoroethanesulfonate (4.28 g) was added thereto in small amounts, and stirred at 25° C. for 1 hour. After the completion of the reaction, the dichloromethane solution was washed with water, and then concentrated and dried. The resulting powder was dispersed and washed in hexane, followed by drying under reduced pressure, thereby obtaining 7.23 g of the objective compound (yield: 90.2%).

The obtained compound was analyzed by $^1$H-NMR and $^{19}$F-NMR.

$^1$H-NMR (DMSO-d6, 600MHz): δ(ppm)=7.97(s, 1H, H$^c$), 7.94-7.91(m, 3H, phenyl+naphthyl), 7.83-7.81(m, 2H, phenyl+naphthyl), 7.76-7.75(m, 8H, phenyl+naphthyl), 7.55-7.52(m, 3H, phenyl+naphthyl), 7.496(s, 2H, H$^d$), 5.21 (s, 2H, H$^b$), 2.24(s, 6H, H$^a$).

$^{19}$F-NMR (Acetone-d6, 376MHz): δ(ppm)=−82.8, −115.8

From the results shown above, it was confirmed that the compound had a structure shown below.

[Chemical Formula 54.]

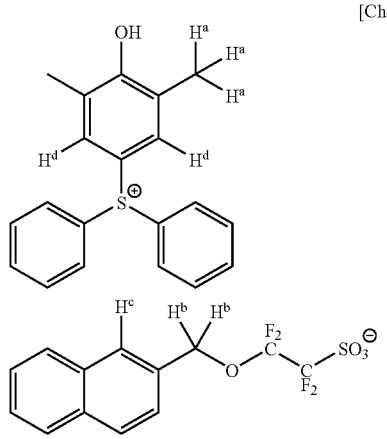

Example 1

Synthesis of Compound (b1-14-101)

[Chemical Formula 55.]

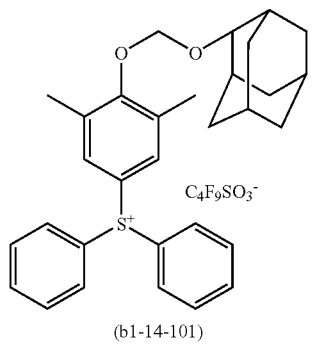

(b1-14-101)

Compound (1) (12.1 g) was dissolved in dichloromethane (54.6 g) and water (60.4 g). Then, potassium nonafluoro-n-butanesulfonate (11.2 g) was added thereto, and stirred at room temperature for 1 hour. Thereafter, the resultant was subjected to liquid separation, and the organic phase was washed with water, and then concentrated and dried, thereby obtaining 16.5 g of a compound which is the compound (1) having the anion replaced by nonafluoro-n-butanesulfonate anion. The obtained compound (6.1 g) was dissolved in 80.9 g of dehydrated tetrahydrofuran, and cooled with ice to 10° C. or lower. Then, sodium hydride (0.44 g) was added thereto, and a tetrahydrofuran (4.4 g) solution of 2-adamantanechloromethylether (2.2 g) was dropwise added thereto. The resultant was elevated to room temperature and stirred for 1 hour. Thereafter, the reaction liquid was dropwise added to water, and the resulting solution was extracted with dichloromethane (90 g). The dichloromethane phase was washed with diluted hydrochloric acid-water, followed by washing with water. The resulting dichloromethane solution was dropwise added to hexane (150 g), thereby obtaining 6.9 g of the objective compound in the form of a white powder.

The obtained compound was analyzed by $^1$H-NMR and $^{19}$F-NMR.

$^1$H-NMR(DMSO-d6, 400 MHz): δ(ppm)=7.76-7.88(m, 10H, H$^a$-H$^e$), 7.60(s, 2H, H$^f$), 5.24(s, 2H, H$^g$), 3.88(s, 1H, H$^h$), 2.33(s, 6H, H$^i$), 1.46-1.99(m, 14H, Adamantane).

$^{19}$F-NMR(DMSO-d6, 376MHz): δ(ppm)=−80.4, −114.6, −121.1, −125.3.

From the results shown above, it was confirmed that the compound had a structure shown below.

[Chemical Formula 56.]

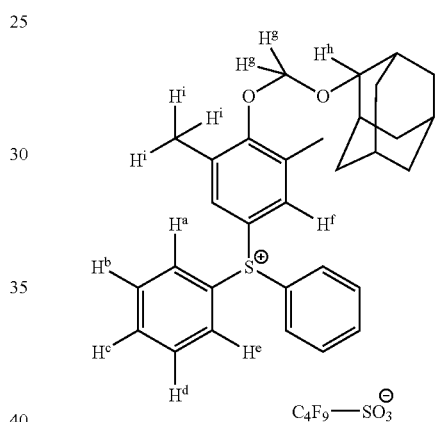

Example 2

Synthesis of Compound (b1-14-201)

[Chemical Formula 57.]

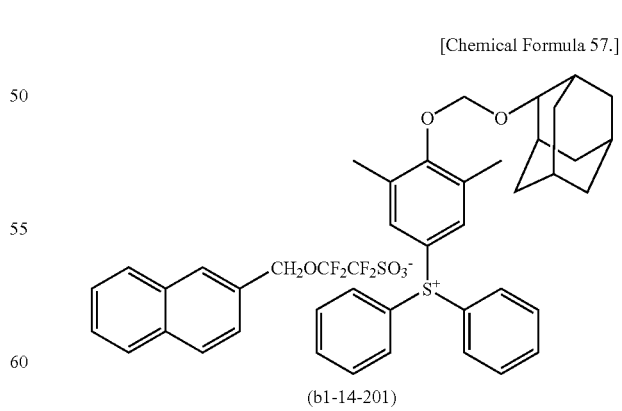

(b1-14-201)

5.00 g of the compound (2) was added to 75 ml of a tetrahydrofuran solution, and cooled with ice. Then, 0.34 g of sodium hydride was added thereto, and a tetrahydrofuran (3.42 ml) solution of 2-adamantanedichloromethylether (1.713 g) was dropwise added thereto. The resultant was elevated to room temperature and stirred for 1 hour. Thereafter, the reaction liquid was dropwise added to water, and the resulting solution was extracted with dichloromethane (60.4 g). The dichloromethane phase was washed with diluted hydrochloric acid-water, followed by washing with water. Then, the dichloromethane solution was concentrated and dried, and the resulting powder was dispersed in hexane. The dispersion was dried under reduced pressure, thereby obtaining 4.27 g of the objective compound (yield: 68.1%).

The obtained compound was analyzed by $^1$H-NMR and $^{19}$F-NMR.

$^1$H-NMR(DMSO-d6, 600MHz): δ(ppm)=7.89(s, 1H, H$^e$), 7.87-7.59(m, 13H, phenyl+naphthyl), 7.561(s, 2H, H$^e$), 7.54-7.52(m, 3H, phenyl+naphthyl), 5.23-5.21(d, 4H, H$^d$), 3.87(s, 1H, H$^f$), 2.33(s, 6H, H$^a$), 1.99-1.45(m, 14H, Adamantane).

$^{19}$F-NMR(Acetone-d6, 376MHz): δ(ppm)=−82.9, −115.9.

From the results shown above, it was confirmed that the compound had a structure shown below.

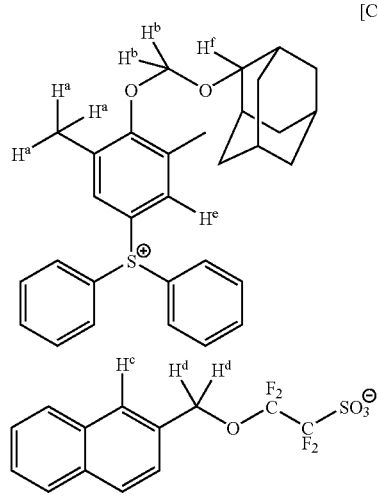

[Chemical Formula 58.]

Example 3

Synthesis of Compound (b1-14-301)

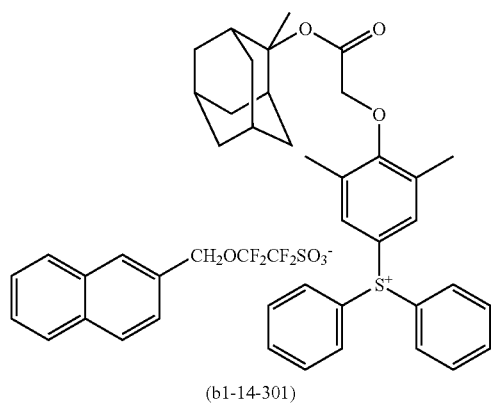

[Chemical Formula 59.]

(b1-14-301)

Substantially the same procedure as in Example 2 was performed, except that 2-adamantanedichloromethylether was changed to 2-methyl-2adamantane bromoacetate in a molar equivalent amount.

The obtained compound was analyzed by $^1$H-NMR and $^{19}$F-NMR.

$^1$H-NMR(CDCl$_3$, 400MHz): δ(ppm)=7.84(s, 1H, H$^f$), 7.71-7.77(m, 3H, Phenyl+Naphthyl), 7.57-7.67(m, 10H, Phenyl+Naphthyl), 7.39-7.51(m, 3H, Phenyl+Naphthyl), 7.36(s, 2H, H$^d$), 5.19(s, 2H, H$^c$), 4.38(s, 2H, H$^b$), 2.32(s, 6H, H$^a$), 1.69-1.97(m, 11H, Adamantane), 1.66(s, 3H, H$^e$), 1.55-1.58(d, 3H, Adamantane).

$^{19}$F-NMR(CDCl$_3$, 400MHz): δ(ppm)=−76.87, −109.14.

From the results shown above, it was confirmed that the compound had a structure shown below.

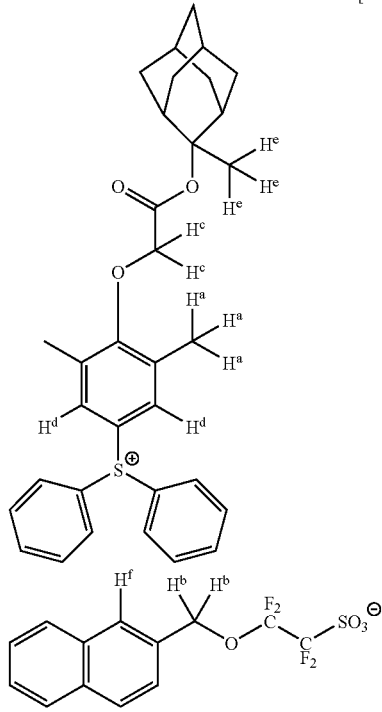

[Chemical Formula 60.]

Examples 4 to 6 and Comparative Example 1

Preparation of Positive Resist Composition

The components shown in Table 1 were mixed together and dissolved to obtain positive resist compositions.

TABLE 1

| | Component (A) | Component (B) | Component (D) | Component (S) |
|---|---|---|---|---|
| Example 4 | (A)-1 [100] | (B)-1 [6.77] | (D)-1 [0.10] | (S)-1 [2200] |
| Example 5 | (A)-1 [100] | (B)-2 [7.10] | (D)-1 [0.10] | (S)-1 [2200] |
| Example 6 | (A)-1 [100] | (B)-3 [6.90] | (D)-1 [0.10] | (S)-1 [2200] |
| Comp. Ex. 1 | (A)-1 [100] | (B)-4 [4.94] | (D)-1 [0.10] | (S)-1 [2200] |

In Table 1, the reference characters indicate the following. Further, the values in brackets [ ] indicate the amount (in terms of parts by weight) of the component added.

(A)-1: a polymer represented by chemical formula (A)-1 shown below (B)-1: an acid generator represented by chemical formula (b1-14-101) above (compound of Example 1)

(B)-2: an acid generator represented by chemical formula (b1-14-201) above (compound of Example 2)

(B)-3: an acid generator represented by chemical formula (b1-14-301) above (compound of Example 3)

(B)-4: triphenylsulfonium nonafluoro-n-butanesulfonate (D)-1: tri-n-pentylamine (S)-1: a mixed solvent of PGMEA/PGME=6/4 (weight ratio)

(B)-1 to (B)-4 are in molar equivalent amounts

[Chemical Formula 61.]

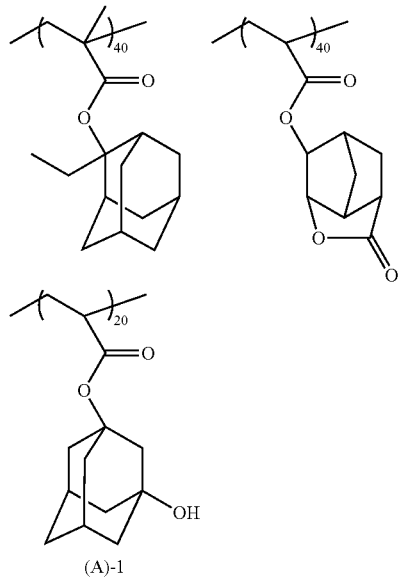

(A)-1

[Mw=7,000, Mw/Mn=2.0]

<Evaluation of Lithography Properties>

Using the obtained positive resist composition solutions, resist patterns were formed, and the following lithography properties were evaluated.

[Resolution·Sensitivity]

An organic anti-reflection film composition (product name: ARC29, manufactured by Brewer Science Ltd.) was applied onto an 8-inch silicon wafer using a spinner, and the composition was then baked at 205° C. for 60 seconds, thereby forming an organic anti-reflection film having a film thickness of 89 nm. Then, a positive resist composition solution obtained above was applied onto the anti-reflection film using a spinner, and was then prebaked (PAB) on a hotplate at 100° C. for 60 seconds and dried, thereby forming a resist film having a film thickness of 120 nm.

Subsequently, a coating solution for forming a protection film (product name: TSRC-002; manufactured by Tokyo Ohka Kogyo Co., Ltd.) was applied onto the resist film using a spinner, and then heated at 90° C. for 60 seconds, thereby forming a top coat with a film thickness of 28 nm.

Thereafter, using an ArF exposure apparatus NSR-S609B (manufactured by Nikon Corporation, NA (numerical aperture)=1.07, ⅔ annular illumination), the resist film having a top coat formed thereon was selectively irradiated with an ArF excimer laser (193 nm) through a mask having a hole pattern (bias: 0 nm) in which holes having a hole diameter (CD) of 75 nm are equally spaced (pitch: 131 nm).

Next, the top coat was removed using a protection-film removing solution (product name: TS-Rememover-S; manufactured by Tokyo Ohka Kogyo Co., Ltd.). Then, a post exposure bake (PEB) treatment was conducted at 95° C. for 60 seconds, followed by development for 30 seconds at 23° C. in a 2.38% by weight aqueous solution of tetramethylammonium hydroxide (product name: NMD-W; manufactured by Tokyo Ohka Kogyo Co., Ltd.). Then, the resist film was rinsed for 30 seconds with pure water, followed by drying by shaking.

As a result, a contact hole pattern in which holes having a hole diameter (CD) of 70 nm are equally spaced (pitch: 131 nm) was formed on the resist film.

Further, the optimum exposure dose (sensitivity: Eop, mJ/cm$^2$) with which the hole pattern was formed was determined. As a result, it was found that the optimum exposure dose was 61 mJ/cm$^2$ in Example 4, 85 mJ/cm$^2$ in Example 5, 57 mJ/cm$^2$ in Example 6, and 34 mJ/cm$^2$ in Comparative Example 1.

[Pattern Shape]

The C/H pattern having a hole diameter of 70 nm and a pitch of 131 nm was observed by a scanning electron microscope (product name: S-9220, manufactured by Hitachi, Ltd.). As a result, it was found that the removability (ability to allow substantially equivalent holes to be formed) of the C/H patterns formed in Examples 4 to 6 was superior to the C/H pattern formed in Comparative Example 1. Further, with respect to the C/H pattern formed in Comparative Example 1, it was confirmed that some portions of the resist film were not completely removed from the holes (substantially equivalent holes could not be formed).

[Evaluation of Mask Error Factor (MEF)]

With the above-mentioned Eop, C/H patterns were formed using a mask pattern targeting a C/H pattern having a hole diameter of 70 nm and a pitch of 131 nm, and a mask pattern targeting a C/H pattern having a hole diameter of 75 nm and a pitch of 131 nm. With respect to the formed C/H patterns, the MEF was determined by the following formula.

$$MEF=|CD_{75}-CD_{70}|/|MD_{75}-MD_{70}|$$

In this formula, $CD_{75}$ and $CD_{70}$ represent the respective diameters (nm) of the actual holes of the C/H patterns respectively formed using the mask pattern targeting a hole diameter of 75 nm and the mask pattern targeting a hole diameter of 70 nm, and MD75 and $MD_{70}$ represent the respective target hole diameters (nm), meaning $MD_{75}$=75 and $MD_{70}$=70.

The MEF is a parameter that indicates how faithfully mask patterns of differing dimensions can be reproduced by using the same exposure dose with fixed pitch and changing the mask size (the hole diameter of a C/H pattern or the line width of a line and space pattern). The closer the MEF value is to 1, the better the mask reproducibility. As a result of the evaluation, it was confirmed that the mask reproducibility was excellent in Examples 4 to 6, as compared to Comparative Example 1.

[Evaluation of CD Uniformity (CDU)]

With respect to each of the C/H patterns formed with the above-mentioned Eop, the hole diameter (CD) of 25 holes were measured, and from the results, the value of 3 times the standard deviation a (i.e., 3σ) was calculated as a yardstick of CD uniformity (CDU). The smaller this 3σ value is, the higher the level of CDU of the holes formed in the resist film.

As a result of the evaluation, it was found that 3σ was 13.65 in Example 4, 14.51 in Example 5, 11.99 in Example 6, and 16.60 in Comparative Example 1.

[Evaluation of Circularity]

Each of the C/H patterns formed with the above-mentioned Eop was observed from the upper side thereof using a scanning electron microscope (product name: S-9220, manufactured by Hitachi, Ltd.), and with respect to each of 25 holes, the distance from the center of the hole to the outer periphery thereof was measured in 24 directions. From the results, the value of 3 times the standard deviation σ (i.e., 3σ) was calculated as a yardstick of circularity. The smaller this 3a value is, the higher the level of circularity of the holes.

As a result of the evaluation, it was found that 3σ was 5.5 in Example 4, 4.7 in Example 5, 4.1 in Example 6, and 5.2 in Comparative Example 1. Therefore, in Example 4 and Comparative Example 1, the circularity was substantially the same. Further, in Examples 5 and 6, the circularity was superior to that in Comparative Example 1.

From the results shown above, it was confirmed that a resist composition containing the acid generator of the present invention is advantageous in that the pattern shape is satisfactory, and exhibits excellent MEF, CDU and circularity, and hence, exhibits excellent lithography properties as compared to resist compositions containing a conventional acid generator.

Example 7

Synthesis of Compounds (b1-14-501) to (b1-14-503)

[Chemical Formula 62.]

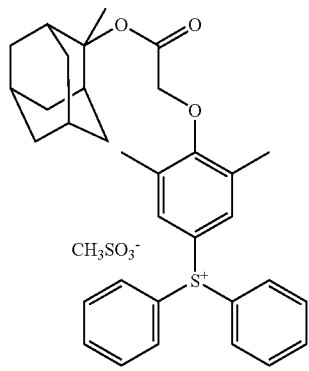

(b1-14-501)

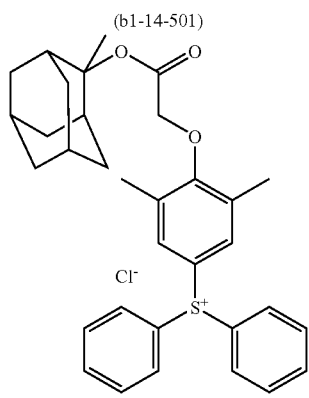

(b1-14-502)

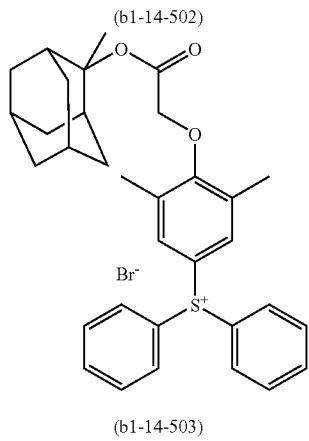

(b1-14-503)

The compound (1) (4 g) was dissolved in dichloromethane (79.8 g). After confirming that the compound (1) had dissolved, potassium carbonate (6.87 g) was added thereto, and 2-methyl-2-adamantane bromoacetate (3.42 g) was further added. A reaction was effected under reflux for 24 hours, followed by filtration, washing with water, and crystallizing with hexane. The resulting powder was dried under reduced pressure, thereby obtaining 3.98 g of the objective compound (yield: 66%).

The obtained compound was analyzed by $^1$H-NM. The results are shown below.

$^1$H-NMR(CDCl$_3$, 600MHz): δ(ppm)=7.83-7.86(m, 4H, phenyl), 7.69-7.78(m, 6H, phenyl), 7.51(s, 2H, Hd), 4.46(s, 2H, Hc), 2.39(s, 6H, Ha), 2.33(s, 2H, Adamantane 2.17(s, 2H, Adamantane), 1.71-1.976(m, 11H, Adamantane), 1.68(s, 3H, Hb), 1.57-1.61(m, 2H, Adamantane).

From the results shown above, it was confirmed that the obtained compound contained a compound (b1-14-501) having the structure shown below. Further, as a result of ion chromatography measurement, it was confirmed that the obtained compound also contained a compound (b1-14-502) and a compound (b1-14-503) which show the same NMR data for the cation moiety as the NMR data shown above. The ratio (mol %) of these compounds were 21.4 mol % for the compound (b1-14-501), 11.4 mol % for the compound (b1-14-502), and 67.2 mol % for the compound (b1-14-503).

[Chemical Formula 63.]

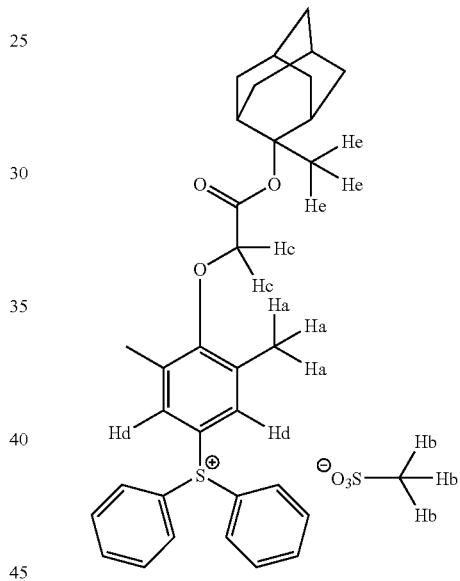

Example 8

Synthesis of Compound (b1-14-401)

[Chemical Formula 64.]

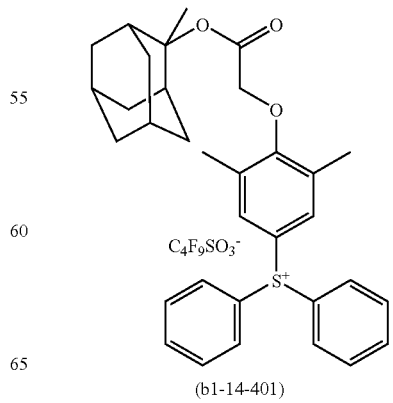

(b1-14-401)

25.5 g of the mixture of 21.4 mol % of the compound (b1-14-501), 11.4 mol % of the compound (b1-14-502) and 67.2 mol % of the compound (b1-14-503) was dissolved in 200 g of pure water. Dichloromethane (127.4 g) and potassium nonafluoro-n-butanesulfonate (16.0 g) were added thereto, and stirred at room temperature for 14 hours. Thereafter, the dichloromethane phase was separated, and washed with diluted hydrochloric acid, ammonia and water in this order. Then, the dichloromethane phase was concentrated and dried, thereby obtaining the objective compound (32.9 g) in the form of a white solid.

The obtained compound was analyzed by $^1$H-NMR and $^{19}$F-NMR.

$^1$H-NMR(DMSO-d6, 400MHz): δ(ppm)=7.75-7.86(m, 10H, ArH), 7.61(s, 2H, ArH), 4.62(s, 2H, CH$_2$), 2.31(s, 6H, CH$_3$), 1.49-1.97(m, 17H, Adamantane).

$^{19}$F-NMR(DMSO-d6, 376MHz): δ(ppm)=−77.8,-112.2,-118.7,-123.0.

From the results, it was confirmed that the compound had the structure as shown above.

Example 9

Synthesis of Compound (b1-14-402)

[Chemical Formula 65.]

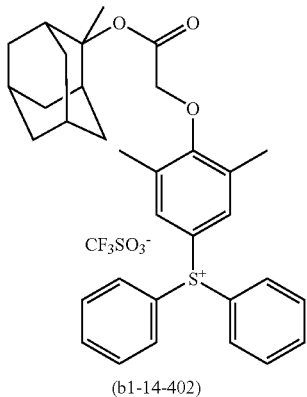

(b1-14-402)

8.93 g of the mixture of 21.4 mol % of the compound (b1-14-501), 11.4 mol % of the compound (b1-14-502) and 67.2 mol % of the compound (b1-14-503) was dissolved in 70.4 g of pure water. Dichloromethane (44.7 g) and potassium trifluoromethanesulfonate (3.12 g) were added thereto, and stirred at room temperature for 14 hours. Thereafter, the dichloromethane phase was separated, and washed with diluted hydrochloric acid, ammonia and water in this order. Then, the dichloromethane phase was concentrated and dried, thereby obtaining the objective compound (8.70 g) in the form of a white solid.

The obtained compound was analyzed by $^1$H-NMR and $^{19}$F-NMR.

$^1$H-NMR(DMSO-d6, 400MHz): δ(ppm)=7.74-7.86(m, 10H, ArH), 7.60(s, 2H, ArH), 4.62(s, 2H, CH$_2$), 2.31(s, 6H, CH$_3$), 1.49-1.97(m, 17H, Adamantane).

$^{19}$F-NMR(DMSO-d6, 376MHz): δ(ppm)=−75.2.

From the results, it was confirmed that the compound had the structure as shown above.

Examples 10 to 17 and Comparative Example 2

Preparation of Positive Resist Composition

The components shown in Table 2 were mixed together and dissolved to obtain positive resist compositions.

TABLE 2

| | Component (A) | Component (B) | Component (D) | Component (S) |
|---|---|---|---|---|
| Example 10 | (A)-2 [100] | (B)-5 [11.5] | (D)-1 [1.2] | (S)-1 [2200] |
| Example 11 | (A)-3 [100] | (B)-5 [11.5] | (D)-1 [1.2] | (S)-1 [2200] |
| Example 12 | (A)-2 [80] (A)-4 [20] | (B)-5 [11.5] | (D)-1 [1.2] | (S)-1 [2200] |
| Example 13 | (A)-2 [60] (A)-4 [40] | (B)-5 [11.5] | (D)-1 [1.2] | (S)-1 [2200] |
| Example 14 | (A)-2 [100] | (B)-1 [9.6] (B)-6 [1.0] | (D)-1 [1.2] | (S)-1 [2200] |
| Example 15 | (A)-2 [100] | (B)-1 [5.6] (B)-6 [3.0] | (D)-1 [1.2] | (S)-1 [2200] |
| Example 16 | (A)-2 [100] | (B)-1 [9.2] (B)-7 [1.9] | (D)-1 [1.2] | (S)-1 [2200] |
| Example 17 | (A)-2 [100] | (B)-1 [6.9] (B)-7 [3.8] | (D)-1 [1.2] | (S)-1 [2200] |
| Comparative Example 2 | (A)-2 [100] | (B)-8 [8.0] | (D)-1 [1.2] | (S)-1 [2200] |

In Table 2, the reference characters indicate the following. Further, the values in brackets [ ] indicate the amount (in terms of parts by weight) of the component added.

(A)-2: a polymer represented by chemical formula (A)-2 shown below (Mw=7,000, Mw/Mn=1.8)

(A)-3: a polymer represented by chemical formula (A)-2 shown below (Mw=10,000, Mw/Mn 2.0)

(A)-4: a polymer represented by chemical formula (A)-4 shown below (Mw=5,000, Mw/Mn=1.5)

(B)-5: an acid generator represented by chemical formula (b1-14-401) above (compound of Example 8)

(B)-6: triphenylsulfonium trifluoromethanesulfonate (B)-7: di(1-naphthyl)phenylsulfonium nonafluoro-n-butanesulfonate (B)-8: 4-methylphenyldiphenylsulfonium nonafluoro-n-butanesulfonate

[Chemical Formula 66.]

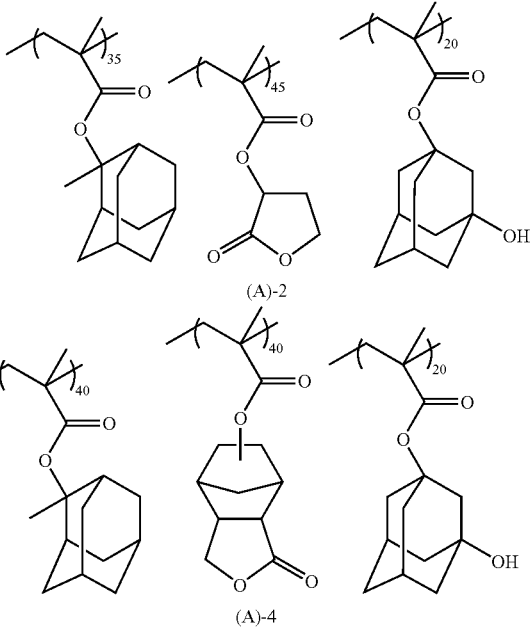

(A)-2

(A)-4

95

<Evaluation of Lithography Properties>

Using the obtained positive resist composition solutions, resist patterns were formed, and the following lithography properties were evaluated.

[Resolution·Sensitivity]

An organic anti-reflection film composition (product name: ARC29, manufactured by Brewer Science Ltd.) was applied onto an 8-inch silicon wafer using a spinner, and the composition was then baked at 205° C. for 60 seconds, thereby forming an organic anti-reflection film having a film thickness of 75 nm. Then, a positive resist composition solution obtained above was applied onto the anti-reflection film using a spinner, and was then prebaked (PAB) on a hotplate at 100° C. for 60 seconds and dried, thereby forming a resist film having a film thickness of 120 nm.

Subsequently, using an ArF exposure apparatus NSR-S609B (manufactured by Nikon Corporation, NA (numerical aperture)=1.07, illumination condition=X-pole (0.78/0.97), polarization condition w/P), the resist film was selectively irradiated with an ArF excimer laser (193 nm) through a mask pattern (6% halftone). Then, a post exposure bake (PEB) treatment was conducted at 110° C. for 60 seconds, followed by development for 40 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist film was rinsed for 40 seconds with pure water, followed by drying by shaking.

As a result, in each of the examples using the respective positive resist compositions, a line and space pattern (L/S pattern) having a line width of 65 nm and a pitch of 130 nm was formed.

Further, the optimum exposure dose (sensitivity: Eop, mJ/cm$^2$) with which the L/S pattern was formed was determined. The results are shown in Table 3.

[Evaluation of MEF]

With the above-mentioned Eop, L/S patterns were formed using mask patterns targeting L/S patterns having a line width of 61 nm, 63 nm, 65 nm, 67 nm and 69 nm, and a pitch of 130 nm. A line was plotted, taking the target size (nm) as the horizontal axis, and the line width (nm) of the pattern formed on the resist film using various mask patterns as the vertical axis. The slope of the plotted line was determined as the MEF. The closer the MEF value (value of the slope of the line) is to 1, the better the mask reproducibility. The results are shown in Table 3.

96

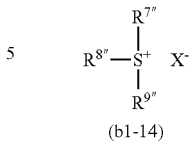

(b1-14)

[Chemical Formula 1]

wherein $R^{7\prime\prime}$ to $R^{9\prime\prime}$ each independently represents an aryl group or an alkyl group, wherein two of $R^{7\prime\prime}$ to $R^{9\prime\prime}$ may be bonded to each other to form a ring with the sulfur atom, and at least one of $R^{7\prime\prime}$ to $R^{9\prime\prime}$ represents a substituted aryl group in which a portion or all of the hydrogen atoms are substituted with an alkoxyalkyloxy group represented by general formula (b14-1) shown below or an alkoxycarbonylalkyloxy group represented by general formula (b14-2) shown below; and $X^-$ represents an anion:

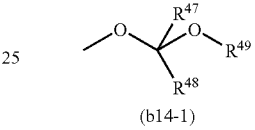

(b14-1)

[Chemical Formula 2]

wherein $R^{47}$ and $R^{48}$ each independently represents a hydrogen atom or a linear or branched alkyl group, with the proviso that at least one of $R^{47}$ and $R^{48}$ represents a hydrogen atom; and $R^{49}$ represents an alkyl group, wherein $R^{48}$ and $R^{49}$ may be bonded to each other to form a ring structure; and

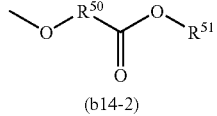

(b14-2)

[Chemical Formula 3]

TABLE 3

|  | Ex. 10 | Ex. 11 | Ex. 12 | Ex. 13 | Ex. 14 | Ex. 15 | Ex. 16 | Ex. 17 | Comp. Ex. 2 |
|---|---|---|---|---|---|---|---|---|---|
| Eop (mJ/cm$^2$) | 27.0 | 29.9 | 28.8 | 31.6 | 29.0 | 26.5 | 32.5 | 38.0 | 23.5 |
| MEF | 3.29 | 3.3 | 3.49 | 3.43 | 3.76 | 3.69 | 3.22 | 3.28 | 3.92 |

From the results shown above, it was confirmed that the resist compositions of Examples 10 to 17 containing an acid generator of the present invention exhibited excellent mask reproducibility, as compared to the resist composition of Comparative Example 2.

The invention claimed is:

1. A resist composition comprising a base component (A) which exhibits changed solubility in an alkali developing solution under action of acid and an acid-generator component (B) which generates acid upon exposure, said acid-generator component (B) comprising an acid generator (B1) consisting of a compound represented by general formula (b1-14) shown below:

wherein $R^{50}$ represents a linear or branched alkylene group; and $R^{51}$ represents a cyclic tertiary alkyl ester-type acid dissociable group.

2. The resist composition according to claim 1, wherein said base component (A) is a base component which exhibits increased solubility in an alkali developing solution under action of acid.

3. The resist composition according to claim 2, wherein said base component (A) is a resin component (A1), and has a structural unit (a1) derived from an acrylate ester containing an acid dissociable, dissolution inhibiting group.

4. The resist composition according to claim 3, wherein said base component (A) further has a structural unit (a2) derived from an acrylate ester having a lactone-containing cyclic group.

5. The resist composition according to claim 3, wherein said base component (A) further has a structural unit (a3) derived from an acrylate ester containing a polar group-containing aliphatic hydrocarbon group.

6. The resist composition according to claim 4, wherein said base component (A) further has a structural unit (a3) derived from an acrylate ester containing a polar group-containing aliphatic hydrocarbon group.

7. The resist composition according to claim 1, which further comprises a nitrogen-containing organic compound (D).

8. A method of forming a resist pattern, comprising:
applying a resist composition of claim 1 to a substrate to form a resist film on the substrate; conducting exposure of said resist film; and alkali-developing said resist film to form a resist pattern.

9. A compound represented by general formula (b1-14) shown below:

[Chemical Formula 4]

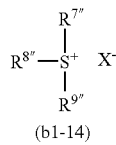

(b1-14)

wherein $R^{7'''}$ to $R^{9'''}$ each independently represents an aryl group or an alkyl group, wherein two of $R^{7'''}$ to $R^{9'''}$ may be bonded to each other to form a ring with the sulfur atom, and at least one of $R^{7'''}$ to $R^{9'''}$ represents a substituted aryl group in which a portion or all of the hydrogen atoms are substituted with an alkoxyalkyloxy group represented by general formula (b14-1) shown below or an alkoxycarbonylalkyloxy group represented by general formula (b14-2) shown below; and $X^-$ represents an anion:

[Chemical Formula 5]

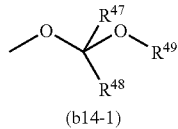

(b14-1)

wherein $R^{47}$ and $R^{48}$ each independently represents a hydrogen atom or a linear or branched alkyl group, with the proviso that at least one of $R^{47}$ and $R^{48}$ represents a hydrogen atom; and $R^{49}$ represents an alkyl group, wherein $R^{48}$ and $R^{49}$ may be bonded to each other to form a ring structure; and

[Chemical Formula 6]

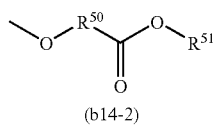

(b14-2)

wherein $R^{50}$ represents a linear or branched alkylene group; and $R^{51}$ represents a cyclic tertiary alkyl ester-type acid dissociable group.

10. An acid generator consisting of a compound of claim 9.

11. The resist composition according to claim 1, wherein said cyclic tertiary alkyl ester-type acid dissociable group is a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group or a 1-ethyl-1-cyclohexyl group.

12. The compound according to claim 9, wherein said cyclic tertiary alkyl ester-type acid dissociable group is a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group or a 1-ethyl-1-cyclohexyl group.

* * * * *